United States Patent
Yodfat et al.

(10) Patent No.: US 8,971,981 B2
(45) Date of Patent: Mar. 3, 2015

(54) DEVICE AND METHOD FOR FACILITATING INFUSION OF THERAPEUTIC FLUIDS AND SENSING OF BODILY ANALYTES

(75) Inventors: Ofer Yodfat, Maccabim-Reut (IL); Iddo M. Gescheit, Tel Aviv (IL); Illai Gescheit, Tel Aviv (IL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 418 days.

(21) Appl. No.: 12/452,928

(22) PCT Filed: Jul. 31, 2008

(86) PCT No.: PCT/IL2008/001059
§ 371 (c)(1),
(2), (4) Date: Jan. 29, 2010

(87) PCT Pub. No.: WO2009/016638
PCT Pub. Date: Feb. 5, 2009

(65) Prior Publication Data
US 2010/0137695 A1    Jun. 3, 2010

Related U.S. Application Data

(60) Provisional application No. 60/963,039, filed on Aug. 1, 2007, provisional application No. 61/008,694, filed on Dec. 21, 2007.

(51) Int. Cl.
*A61B 5/05* (2006.01)
*A61M 5/142* (2006.01)
(Continued)

(52) U.S. Cl.
CPC .......... *A61M 5/14248* (2013.01); *A61B 5/6849* (2013.01); *A61M 5/158* (2013.01); *A61M 5/1723* (2013.01); *A61B 5/14532* (2013.01);
(Continued)

(58) Field of Classification Search
CPC ......... A61M 2005/14252; A61M 2005/14268; A61B 5/14244; A61B 5/14248
USPC ............ 600/309, 344–366; 604/27, 157–158, 604/192, 198, 256, 503, 519, 539, 164.01, 604/164.04, 164.07; 606/130; 16/319, 327; 403/1, 46–47, 61, 66–68
See application file for complete search history.

(56) References Cited

U.S. PATENT DOCUMENTS 2,402,306 A * 6/1946 Turkel ........................... 604/174
4,435,013 A * 3/1984 Arihara ......................... 297/364
(Continued)

FOREIGN PATENT DOCUMENTS

| WO | WO-2004022139 A1 | 3/2004 |
| WO | WO-2006032692 A1 | 3/2006 |
| WO | WO-2007065944 A1 | 6/2007 |

OTHER PUBLICATIONS

International Search Report & Written Opinion for PCT Application No. PCT/IL2008/001059, Nov. 13, 2008.

*Primary Examiner* — Navin Natnithithadha
*Assistant Examiner* — Eric Messersmith
(74) *Attorney, Agent, or Firm* — Roche Diagnostics Operations, Inc.

(57) ABSTRACT

Disclosed is an assembly for use with a portable therapeutic device. The assembly includes a mounting housing securable to skin of a patient, and a cannula subcutaneously insertable through a passageway provided within the housing. The cannula is configured to be inserted subsequent to securing of the housing to the skin of the patient.

37 Claims, 44 Drawing Sheets

(51) Int. Cl.
  *A61B 5/00* (2006.01)
  *A61M 5/158* (2006.01)
  *A61M 5/172* (2006.01)
  *A61B 5/145* (2006.01)
  *A61M 5/178* (2006.01)
  *A61M 5/32* (2006.01)

(52) U.S. Cl.
  CPC ............ *A61M5/1782* (2013.01); *A61M 5/3287* (2013.01); *A61M 2005/1581* (2013.01); *A61M 2005/1585* (2013.01)
  USPC ........................ 600/345; 600/365; 604/164.04

(56) References Cited

U.S. PATENT DOCUMENTS

| | | | |
|---|---|---|---|
| 4,530,262 A * | 7/1985 | Pownall ........................ 81/177.9 |
| 4,562,751 A | 1/1986 | Nason et al. |
| 4,685,903 A | 8/1987 | Cable et al. |
| 4,755,173 A | 7/1988 | Konopka et al. |
| 5,080,653 A | 1/1992 | Voss et al. |
| 5,097,122 A | 3/1992 | Colman et al. |
| 5,176,662 A * | 1/1993 | Bartholomew et al. ....... 604/513 |
| 5,257,980 A | 11/1993 | Van Antwerp et al. |
| 5,299,571 A | 4/1994 | Mastrototaro |
| 5,342,319 A | 8/1994 | Watson et al. |
| 5,374,024 A * | 12/1994 | Williams ........................ 248/514 |
| 5,390,671 A | 2/1995 | Lord et al. |
| 5,391,250 A | 2/1995 | Cheney, II et al. |
| 5,482,473 A | 1/1996 | Lord et al. |
| 5,522,803 A | 6/1996 | Teissen-Simony |
| 5,586,553 A * | 12/1996 | Halili et al. .................... 600/316 |
| 5,851,197 A | 12/1998 | Marano et al. |
| 6,254,586 B1 * | 7/2001 | Mann et al. .................... 604/506 |
| 6,565,509 B1 | 5/2003 | Plante et al. |
| 7,931,615 B2 * | 4/2011 | Fangrow, Jr. ................ 604/93.01 |
| 8,435,211 B2 * | 5/2013 | Yodfat et al. ................ 604/93.01 |
| 2002/0022855 A1 * | 2/2002 | Bobroff et al. ................. 606/185 |
| 2002/0119711 A1 * | 8/2002 | VanAntwerp et al. ........ 439/834 |
| 2003/0208207 A1 * | 11/2003 | Layer .............................. 606/130 |
| 2004/0010207 A1 | 1/2004 | Flaherty et al. |
| 2004/0158207 A1 * | 8/2004 | Hunn et al. ................ 604/164.01 |
| 2004/0162521 A1 | 8/2004 | Bengtsson |
| 2004/0162851 A1 | 8/2004 | Nguyen |
| 2004/0254433 A1 * | 12/2004 | Bandis et al. ................. 600/347 |
| 2005/0015075 A1 * | 1/2005 | Wright et al. ................. 604/535 |
| 2005/0215979 A1 * | 9/2005 | Kornerup et al. ............. 604/539 |
| 2006/0129090 A1 * | 6/2006 | Moberg et al. ............. 604/93.01 |
| 2006/0253085 A1 * | 11/2006 | Geismar et al. ............... 604/272 |
| 2007/0135774 A1 | 6/2007 | Turner et al. |
| 2008/0021375 A1 * | 1/2008 | Burns et al. ...................... 604/27 |
| 2008/0215006 A1 * | 9/2008 | Thorkild ........................ 604/151 |
| 2008/0215035 A1 | 9/2008 | Yodfat et al. |
| 2008/0243051 A1 * | 10/2008 | DeStefano ....................... 604/27 |
| 2008/0319414 A1 | 12/2008 | Yodfat et al. |
| 2008/0319416 A1 | 12/2008 | Yodfat et al. |
| 2009/0062767 A1 * | 3/2009 | Van Antwerp et al. ........ 604/504 |
| 2010/0106088 A1 | 4/2010 | Yodfat et al. |
| 2010/0292651 A1 | 11/2010 | Yodfat et al. |

* cited by examiner

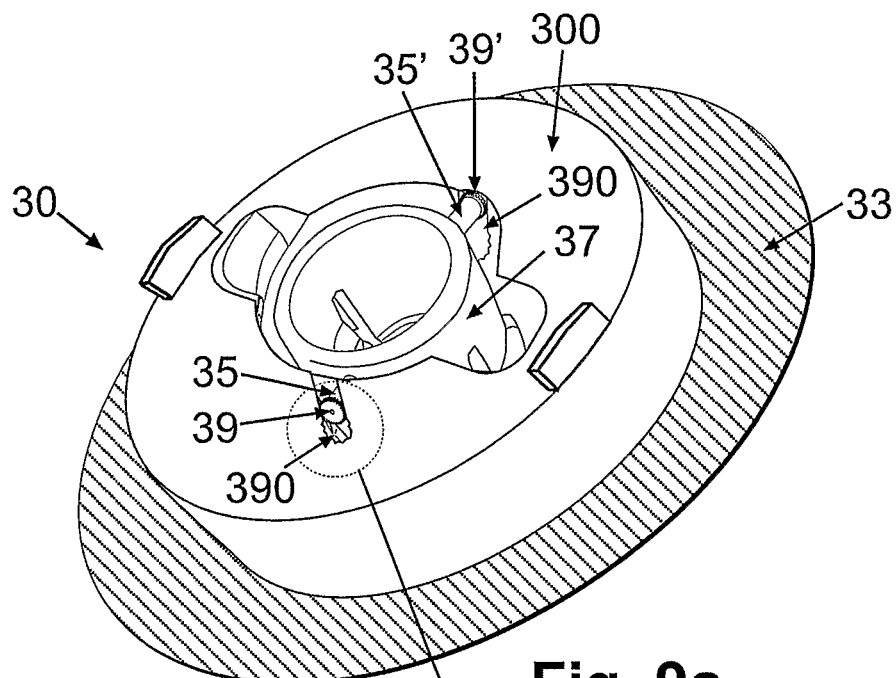
Fig. 9a
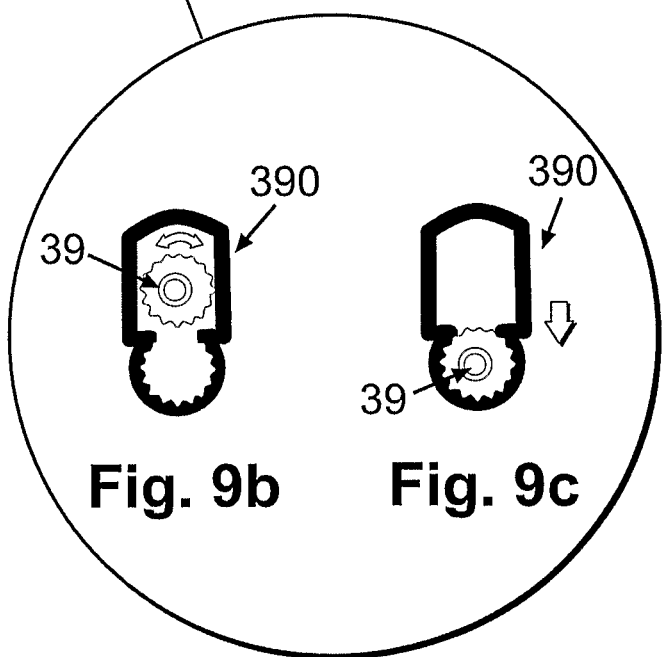
Fig. 9b    Fig. 9c

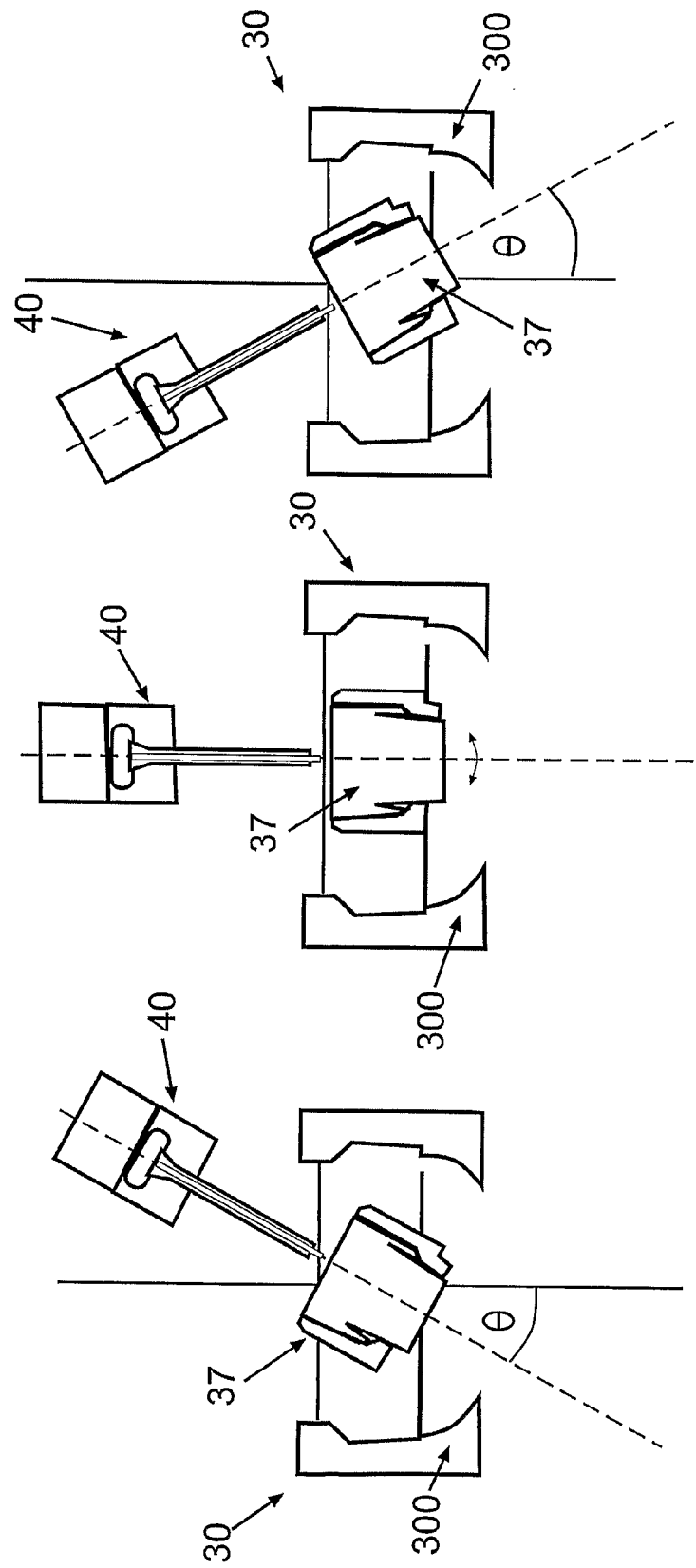

DEVICE AND METHOD FOR FACILITATING INFUSION OF THERAPEUTIC FLUIDS AND SENSING OF BODILY ANALYTES

CROSS-REFERENCE TO RELATED APPLICATIONS

The present application is a 35 U.S.C. §371 national stage entry of PCT/IL2008/001059, which has an international filing date of 31 Jul. 2008 and claims priority to U.S. Provisional Patent Application Nos. 60/963,039, filed on 1 Aug. 2007 and 61/008,694, filed on 21 Dec. 2007. The present application incorporates herein by reference the disclosure of each of the above-referenced applications in its entirety.

BACKGROUND OF THE INVENTION

1. Field of the Invention

The present disclosure relates to a system, a device, an assembly and a method for subcutaneous administration of therapeutic fluid and analyte sensing. More particularly, the present disclosure relates to a soft cannula and a flexible probe and a method for inserting the cannula or probe into the subcutaneous tissue and securing them to the skin. Even more particularly, the present disclosure relates to a cannula or probe that can be easily used with various infusion and sensing devices and mechanisms. Even more particularly, the present disclosure relates to a device for delivery of therapeutic fluid into the subcutaneous tissue and for sensing analytes, and a method for automatic or manual cannula or probe insertion with minimal skin pricking pain.

2. Background

Delivery of Therapeutic Fluids

Transcutaneous injection of therapeutic fluids is usually performed using a rigid (e.g., metal) hypodermic needle on occasion or periodically. Continuous administration of drugs is usually performed using a soft cannula that provides a passageway to the subcutaneous tissue and is connected to an infusion pump with long tubing (the cannula and tubing together are referred to as an "infusion set"). In a common form, the soft cannula is secured to the skin by a housing to include a self-sealing septum mounted at the proximal end of the cannula. The cannula may be initially assembled with an insertion needle (also referred to as "penetrating member") extending through the septum and the cannula. The cannula and the housing can be inserted manually or automatically, as described, for example in U.S. Pat. No. 5,851,197, the content of which is hereby incorporated by reference in its entirety. After piercing the skin, the penetrating member is retracted leaving the soft cannula in place in the patient's subcutaneous compartment. The selected infusion device is then coupled to the cannula, typically by a tubing connected to the infusion pump to deliver the medication through the cannula to the patient. In some embodiments, the tubing is connected to the cannula housing at a distal location from the septum, as shown, for example, in U.S. Pat. Nos. 4,755,173, 5,176,662 and 5,257,980, the contents of which are hereby incorporated by reference in their entireties. In some embodiments, the infusion tubing is coupled to the cannula housing by, for example, an infusion needle that pierces the septum, as discussed, for example, in U.S. Pat. No. 5,522,803, the content of which is hereby incorporated by reference in its entirety. Subcutaneous infusion sets of the above-referenced type are used extensively to continuously deliver drugs such as insulin to the patient in programmable dosages, as discussed, for example, in U.S. Pat. Nos. 4,562,751, 4,685,903, 5,080,653 and 5,097,122, the contents of which are hereby incorporated by reference in their entireties. A soft cannula that provides a passageway to the subcutaneous tissue and is not connected to an infusion pump with long tubing is disclosed in U.S. Patent Application No. 2007/0135774, entitled "Fluid delivery devices, systems and methods", the content of which is hereby incorporated by reference in its entirety. In the above-referenced device, the cannula and housing are rigidly connected to each other and the cannula is inserted manually into the body. After the penetrating member withdrawal, a rubber septum can be repetitively pierced by a needle of a common syringe. This device has some limitations:

1) manual insertion is painful and depends on user skills;
2) vertical insertion angle is generally the only angle feasible; and
3) the rubber septum has to be precisely pierced by the sharp metal needle, which is difficult to accomplish, especially when the device is attached to remote skin sites.

Sensing Bodily Analytes

Performance of continuous or periodic sensing operations of bodily analytes within the interstitial fluid of the subcutaneous ("SC") tissue are discussed, for example, in U.S. Pat. Nos. 5,390,671, 5,391,250, 5,482,473, 5,299,571 and 6,565,509, the contents of which are hereby incorporated by reference in their entireties. Conventional sensing devices include a subcutaneous probe and a sensing unit that contains the processing unit. Insertion mechanisms and devices for SC probes are disclosed, for example, in U.S. Pat. No. 5,586,553, the content of which is hereby incorporated by reference in its entirety. The insertion set includes a penetrating member extending through a mounting base adapted for seated mounting onto the patient's skin. A flexible probe includes a proximal segment carried by the mounting base and a distal segment protruding from the mounting base and having one or more electrodes thereon. When the mounting base is pressed onto the patient's skin, the penetrating member pierces the skin to transcutaneously place the probe's distal segment therein. The penetrating member can then be withdrawn from the mounting base, leaving the probe's distal segment within the patient's body. The above-described probe insertion mechanism has several limitations:

1) the mounting base and the flexible probe are rigidly connected and therefore the insertion has to be performed manually or using a relatively bulky and expensive insertion device ("inserter");
2) insertion is typically painful to the patient; and
3) generally, only one predetermined penetration angle is available.

SUMMARY OF THE INVENTION

Thus, in some embodiments, a soft cannula for delivery of therapeutic fluid into the subcutaneous compartment and a method for inserting the cannula and securing it to the skin are provided.

In some embodiments, multiple deliveries of therapeutic fluid into the body using a syringe at any desired skin site is provided.

In some embodiments, a subcutaneous soft cannula that can be connected to any desired infusion mechanism and/or device is described.

In some embodiments, a subcutaneous soft cannula that can be connected to a portable infusion pump is provided.

In some embodiments, a subcutaneous soft cannula that can be inserted into the body either manually or automatically is provided.

In some embodiments, a subcutaneously soft cannula that can be inserted into the body at any desired angle is described.

In some embodiments, a subcutaneous soft cannula that can be inserted relatively painlessly is provided.

In some embodiments, a soft cannula for delivery of therapeutic fluid into the subcutaneous compartment and a method for inserting the cannula and securing it to the skin are provided.

In some embodiments, a soft cannula for insulin delivery into the subcutaneous compartment and a method for inserting the insulin delivery cannula and securing it to the skin are provided.

In some embodiments, a flexible probe for analyte sensing within the subcutaneous compartment and a method for inserting the probe and securing it to the skin are described.

In some embodiments, a flexible probe for multiple measurements of subcutaneous analytes levels by a sensing device at any desired skin site is provided.

In some embodiments, a subcutaneous flexible probe that can be connected to any desired sensing mechanism/device is provided.

In some embodiments, a subcutaneous flexible probe that can be inserted painlessly is provided.

In some embodiments, a flexible probe for sensing glucose within the subcutaneous compartment and a method for inserting the glucose probe and securing it to the skin are provided.

Some embodiments of the present disclosure relate to a device that facilitates periodic and/or continuous fluid delivery or analyte sensing by avoiding repetitive skin pricking. The device may be secured (e.g., adhered) to the skin for the entire usage duration and may be removably connected to various fluid delivery devices and sensing devices. The device (or assembly) includes two structures (units): a housing that may be initially adhered to the skin and a cannula (or probe) mountable on the housing, and that may be sequentially inserted through a passageway provided within the housing into the subcutaneous compartment. The passageway within the housing (also referred to as a "mounting unit" or a "mounting housing") may be surrounded by anchoring latches that provide a mechanism for vertical or angular cannula (or probe) insertion. After insertion, the cannula (or probe) remains rigidly connected to the housing in a substantially locking configuration. Insertion of the cannula (which is the structure that may include an actual cannula configured to be in fluid communication with the subcutaneous layer of the patient, a cannula hub, a penetrating member, etc.) can be performed manually or automatically with an inserter that may contain a mechanism configured to reduce and/or alleviate pain associated with skin pricking.

In one aspect, a therapeutic fluid delivery device for at least delivering one or more therapeutic fluids to the body of a patient is disclosed. The device includes a housing securable to skin of the patient, and a cannula subcutaneously insertable through a passageway provided within the housing. The cannula is configured to be inserted subsequent to securing of the housing to the skin of the patient.

In another aspect, a bodily analyte sensing device is disclosed. The device includes a housing securable to skin of the patient, and a cannula subcutaneously insertable through a passageway provided within the housing. The cannula is configured to be inserted subsequent to securing of the housing to the skin of the patient.

In a further aspect, a bodily analyte sensing and therapeutic fluid delivery device is disclosed. The device includes a housing securable to skin of the patient, and a cannula subcutaneously insertable through a passageway provided within the housing. The cannula is configured to be inserted subsequent to securing of the housing to the skin of the patient.

Embodiments of any of the above devices may include one or more of the following features.

At least a portion of the cannula may be adapted to rigidly connect to the housing in a locking configuration.

The cannula may be insertable through the passageway at a predetermined angle with respect to a surface of the skin of the patient.

The therapeutic fluid may include insulin.

The analyte may include glucose.

The device(s) may further include an inserter to subcutaneously insert the cannula. The inserter may be configured to reduce resultant pain associated with piercing of the skin of the patient when performing subcutaneous insertion of the cannula. The inserter may be configured to automatically subcutaneously insert the cannula. The inserter may be further configured to automatically retract a penetrating member subsequent to subcutaneous insertion of the cannula.

The cannula may be adapted to be manually subcutaneously inserted.

The housing may include a well defining the passageway. The well may be tiltable relative to a contact surface of the housing that contacts the skin of the patient when the housing is secured to the skin of the patient. The tiltable well may enable insertion of the cannula at an angle. The tiltable well may include a tilting mechanism to control the tilt of the well. The tilting mechanism may include at least one rod attached to the well at one end of the at least one rod and attached at the other end to a gear rotateable within a corresponding groove defined in a base of the housing, the groove having a wide section in which the gear can be rotated, and a narrow section into which the gear is placed to lock the gear and well into place.

The cannula may include a cannula unit that includes a cannula hub attached to the cannula. The cannula unit may further include a rubber septum. The cannula may further include a penetrating member having a grip portion.

The housing may further include one or more anchors to rigidly connect the cannula hub to the housing and positioned proximate the passageway.

The housing may further include an adhesive tape to secure the housing to the body of the patient.

The device(s) may be configured to receive a fluid delivery device connectable to the cannula to enable delivery of the therapeutic fluid to the body of the patient. The fluid delivery device may include one of, for example, a standard syringe, a syringe fitted within an adapter coupleable to an assembly defined by the cannula subcutaneously inserted through the passageway of the housing, a jet pen, a single-part infusion device and/or a two-part infusion device. The housing may further include at least one locking latch to be received in a mating configuration in a complementary at least one recesses defined on the fluid delivery device. The housing may define a concave depression to receive convexed-shaped section of a body of the fluid-delivery device.

The cannula may be further configured to be coupled to a sensing device configured to sense analytes in the body of the patient.

The housing may further include one or more anchors to enable connection and disconnection of another device to and from the housing. The anchors may include at least one latch coupleable to a corresponding at least one complementary recess defined on the other device configured to receive the latch.

The housing may further include an angular adaptor to facilitate fluid injection at an angle.

The housing may further include a connector to establish a connection between a delivery device and the housing.

The housing may be further configured to connect and disconnect to a medical device cradle, the cradle being securable to the user's skin.

The housing may be configured to be fitted with a protective cover connectable to the housing to protect at least the passageway provided in the cannula.

In yet another aspect, an assembly for use with a portable therapeutic device is disclosed. The assembly includes a mounting housing securable to skin of a patient, and a cannula subcutaneously insertable through a passageway provided within the housing. The cannula is configured to be inserted subsequent to securing of the housing to the skin of the patient.

Embodiments of the assembly may include any of the features of any of the devices described above, as well as one or more of the following features.

The assembly may be configured to receive the portable therapeutic device, the portable therapeutic device being coupleable to the cannula to enable performance of a therapeutic procedure. The portable therapeutic device may include a fluid delivery device that may include one or more of, for example, a standard syringe, a syringe fitted within an adapter coupleable to the assembly, a jet pen, a single-part infusion device and/or a two-part infusion device.

The housing may be adapted to facilitate alignment between the housing and the portable therapeutic device to be received by the housing. The housing may further include at least one locking latch to be received in a mating configuration in a complementary at least one recesses defined on the portable therapeutic device. The housing may define a concave depression to receive convexed-shaped section of a body of the portable therapeutic device. The housing may include magnetic material to enable magnetic connection with another magnetic material provided in at least one corresponding connecting area in the portable therapeutic device to be received.

The cannula may be further configured to be coupled to a sensing device configured to determine an analyte in the body of the patient.

The housing may further include one or more anchors to enable connection and disconnection of another device to and from the housing.

The anchors may include at least one latch coupleable to a corresponding at least one complementary recess defined on the other device configured to receive the latch.

The assembly may further include an adapter to connect the portable therapeutic device to the housing. The adapter may include an angular adapter to connect the portable therapeutic device at an angle.

The housing may further include a connector to establish a connection between a delivery device and the housing.

In another aspect, a method for performing a therapeutic procedure on a patient is disclosed. The method includes securing a housing to skin on the body of the patient, the housing defining a passageway providing access to an area of the skin of the patient. The method also includes subcutaneously inserting a cannula through the passageway defined within the housing, penetrating the skin of the patient to subcutaneously place at least part of the cannula in the body of the patient, and performing a therapeutic procedure using the subcutaneously inserted cannula.

Embodiments of the method may include any of the features of any of the devices and the assembly described above, as well as one or more of the following features.

Performing the therapeutic procedure may include one or more of, for example, delivering a therapeutic fluid to the body of the patient and/or sensing a bodily analyte in the body of the patient.

Subcutaneously inserting a cannula through the passageway may include automatically subcutaneously inserting the cannula through the passageway.

Subcutaneously inserting a cannula through the passageway may include reducing resultant pain associated with piercing of the skin of the patient when subcutaneously inserting the cannula.

Subcutaneously inserting a cannula through the passageway may include manually subcutaneously inserting the cannula through the passageway.

Penetrating the skin of the patient to subcutaneously place the at least part of the cannula in the body of the patient may include penetrating the skin of the patient using a penetrating member.

The method may further include automatically retracting the penetrating member after penetrating the skin.

The method may further include rigidly securing at least a portion of the cannula to the housing in a locking configuration subsequent to insertion of the cannula.

The method may further include connecting a portable therapeutic device to the housing for performing the therapeutic procedure.

The method may further include disconnecting the portable therapeutic device from the housing.

In a further aspect, a therapeutic apparatus is discloses. The apparatus includes a portable therapeutic device configured to perform one or more therapeutic operations on a body of a patient, and a therapeutic assembly that includes a housing securable to skin of the patient, and a cannula subcutaneously insertable through a passageway provided within the housing, the cannula being configured to be inserted subsequent to securing of the housing to the skin of the patient. The portable therapeutic device is coupleable to the assembly.

Embodiments of the apparatus may include any of the features of any of the devices, the assembly and the method described above, as well as one or more of the following features.

The portable therapeutic device may include a therapeutic fluid delivery device that includes one of, for example, a standard syringe, a syringe fitted within an adapter coupleable to the assembly, a jet pen, a single-part infusion device and/or a two-part infusion device.

The therapeutic fluid delivery device may include an insulin delivery device.

The portable therapeutic device coupleable to the assembly may include at least one recess to receive in a mating configuration a corresponding at least one complementary locking latch of the assembly to rigidly connect the portable therapeutic device to the assembly.

The assembly may define a concave depression to receive convexed-shaped section of a body of the portable therapeutic device.

The portable therapeutic device may include a sensing device to measure a concentration of a bodily analyte. The bodily analyte may include one or more of, for example, glucose and ketones. The cannula may be further configured to be coupled to a sensor configured to sense analytes in the body of the patient, the sensor further configured to communicate with the sensing device. The sensor may include one or more of, for example, an optical sensor, an electrochemical sensor, an acoustic sensor and/or a Continuous Glucose Monitor (CGM).

The sensor may include at least one electrode, the electrode configured to generate a signal representative of a concentration of the bodily analyte.

At least one of the housing and the cannula may include a communications module to transmit the signal. The communications module may include one or more of, for example, a communications module to communicate via connected wires and/or a wireless transceiver.

BRIEF DESCRIPTION OF THE DRAWINGS

FIGS. 9a-j are views and diagrams of an exemplary housing with a tiltable well.

DETAILED DESCRIPTION OF THE INVENTION

Discloses are devices, apparatus, assemblies and methods for use with a portable therapeutic device. In some embodiments, an assembly that includes a mounting housing securable to skin of a patient and a cannula subcutaneously insertable through a passageway provided within the housing is disclosed. The cannula is configured to be inserted subsequent to securing of the housing to the skin of the patient. As described to herein, the cannula may refer to a cannula, i.e., an insertable member (e.g., a hollow tube, an insertable rod such as a probe, etc.), or it may refer to a cannula assembly (structure, unit or cartridge) that includes the cannula itself as well as additional components used in conjunction with the cannula, including, for example, a cannula hub, a piercing or penetrating member, etc. In some embodiments, the housing is adapted to be coupleable to a portable therapeutic device, such as, for example, a fluid delivery device, a bodily analyte sensing device, etc.

Embodiments for the present disclosure relate to systems, devices, assemblies and methods to facilitate delivery of therapeutic fluid (e.g., insulin) into the subcutaneous compartment by a soft cannula, and further relates to mechanisms to secure the cannula to the patient's skin. In some embodiments, a device and a method to facilitate continuous or periodic sensing of bodily analytes (e.g., glucose) by a subcutaneous probe and mechanisms to secure the probe to the skin are provided. As described herein, the term "cannula" may refer to a "cannula structure" (or "cannula unit", "cannula assembly", "cannula cartridge", etc.) that includes a cannula and may further include additional components (e.g., cannula hub, penetrating member, etc.). The "cannula" may be used to perform such functions as fluid delivery, analyte sensing, etc., and may also be interchangeably referred to as "probe" (i.e., the terms "cannula" and "probe" may be used interchangeably throughout the description and have the same meaning in the present application).

The device and/or assembly described herein may be mounted manually or automatically and may include mechanisms for reducing the pain associated with skin pricking. The device enables fluid delivery to the subcutaneous compartment by various means such as syringe, pump, infusion set or others. The device/assembly may include two structures (or units) that are attached to the body in two stages: a mounting housing (which may be referred to as "housing") that may be first secured (e.g., adhered) to the skin of the patient, and a cannula that may be sequentially inserted through a passageway (defined, for example, by a well) within the housing and into the body. The cannula may be rigidly connected to the housing in a substantially locking configuration.

Figure 1A:
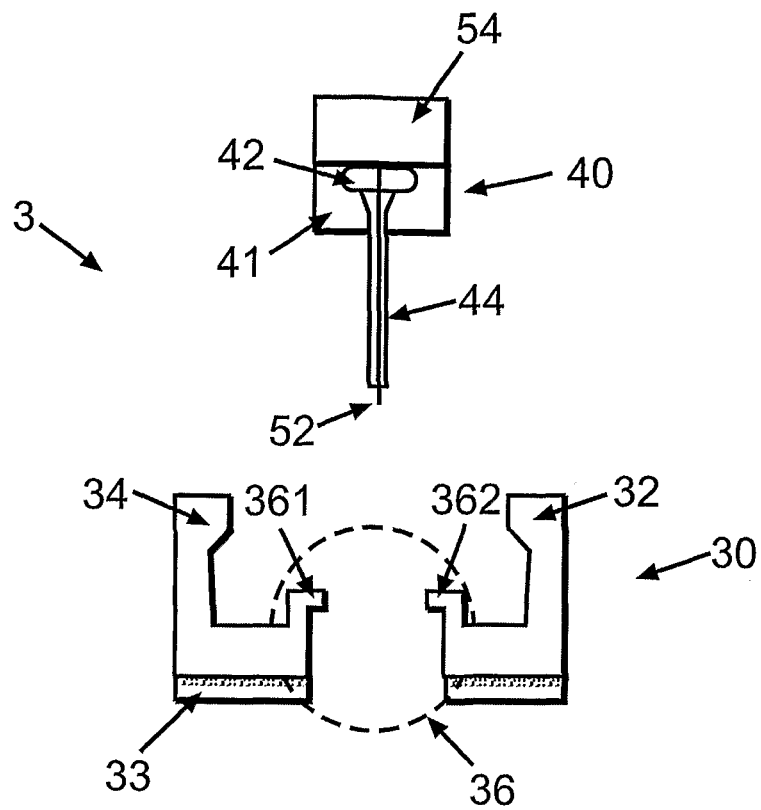
FIGS. 1a-b are schematic diagrams of an exemplary device/assembly of a mounting housing and a cannula.

Referring to FIG. 1a, schematic diagrams of a device (assembly) 3 having a housing (a mounting housing) 30 configured so to enable mounting of another structure thereon and a cannula structure 40 (i.e., the cannula assembly that includes the cannula itself) are shown. In some embodiments, the cannula structure 40 includes a cannula 44, a cannula hub 41 which may be attached to the cannula 44 and may contain a rubber septum 42, and a penetrating member 52 with a grip portion 54. The cannula structure 40 may include a protective cover ("protector") (not shown in FIG. 1a), as detailed below in FIG. 6a, or a smaller protective element (not shown in FIG. 1a), which may be assembled over the cannula 44 and the penetrating member 52 and may be removed prior to use. In some embodiments, the housing 30 includes a passageway 36 (e.g., a tubular passageway) to enable cannula penetration through the mounting housing and into the body. One or more anchoring mechanisms 361 and/or 362, surround the passageway 36 and provides rigid connection of the cannula hub 41 to the housing 30 after cannula insertion. The mounting housing 30 may also include an adhesive tape 33 fixed to the contact surface of the housing (i.e., the surface contacting or closest to the skin) to enable adherence of the housing to the body. The mounting housing 30 may also include one or more latches 32 and/or 34 to enable removable connection of one or more of, for example, a cannula, a probe inserter, a fluid delivery mechanism and/or a sensing mechanism, to the device 3.

Figure 1B:
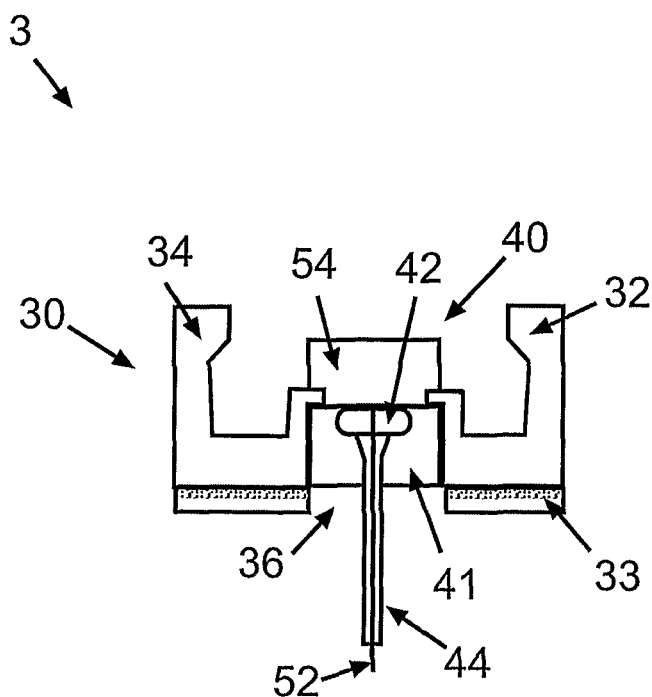

Referring to FIG. 1b, a schematic diagram depicting the exemplary device 3 after connecting the cannula 40 to the mounting housing 30 is shown. In some embodiments, the device 3 includes a single unit (e.g., the cannula and mounting housing are rigidly connected to each other in a locking configuration).

Figure 2A:
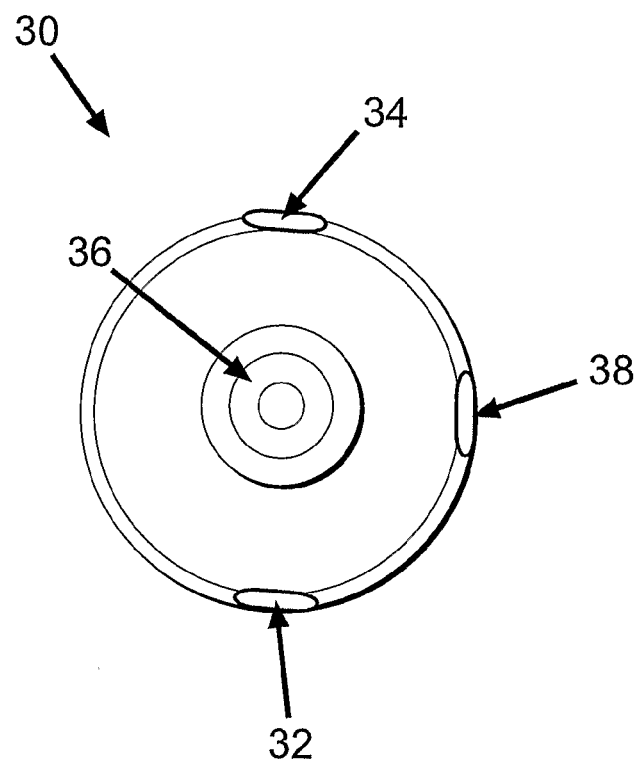
FIGS. 2a-b are views of an exemplary housing to receive a cannula.
Figure 2B:
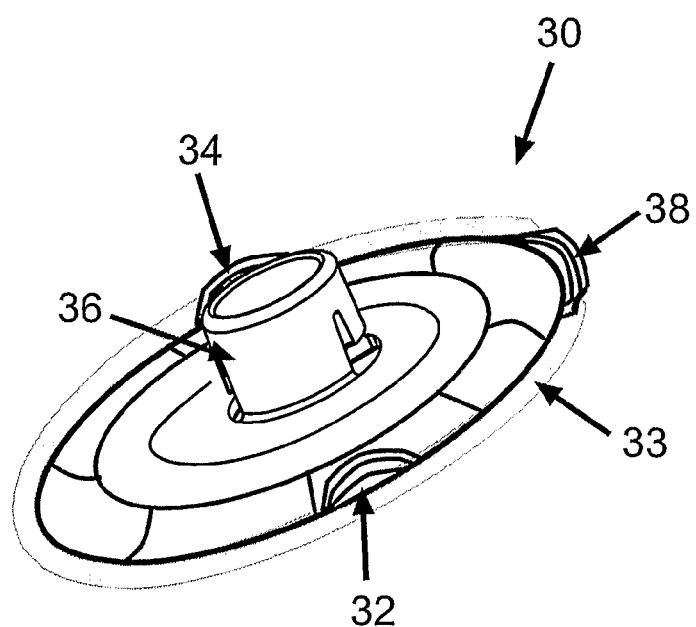

Referring to FIGS. 2a and 2b, a top view and a perspective view, respectively, of a mounting housing 30 having a well defining a passageway 36 and three connecting latches 32, 34 and 38 are shown. An adhesive tape 33 may be attached to the contact surface (which, in some embodiments, is the bottom surface) of the mounting housing 30.

Figure 3:
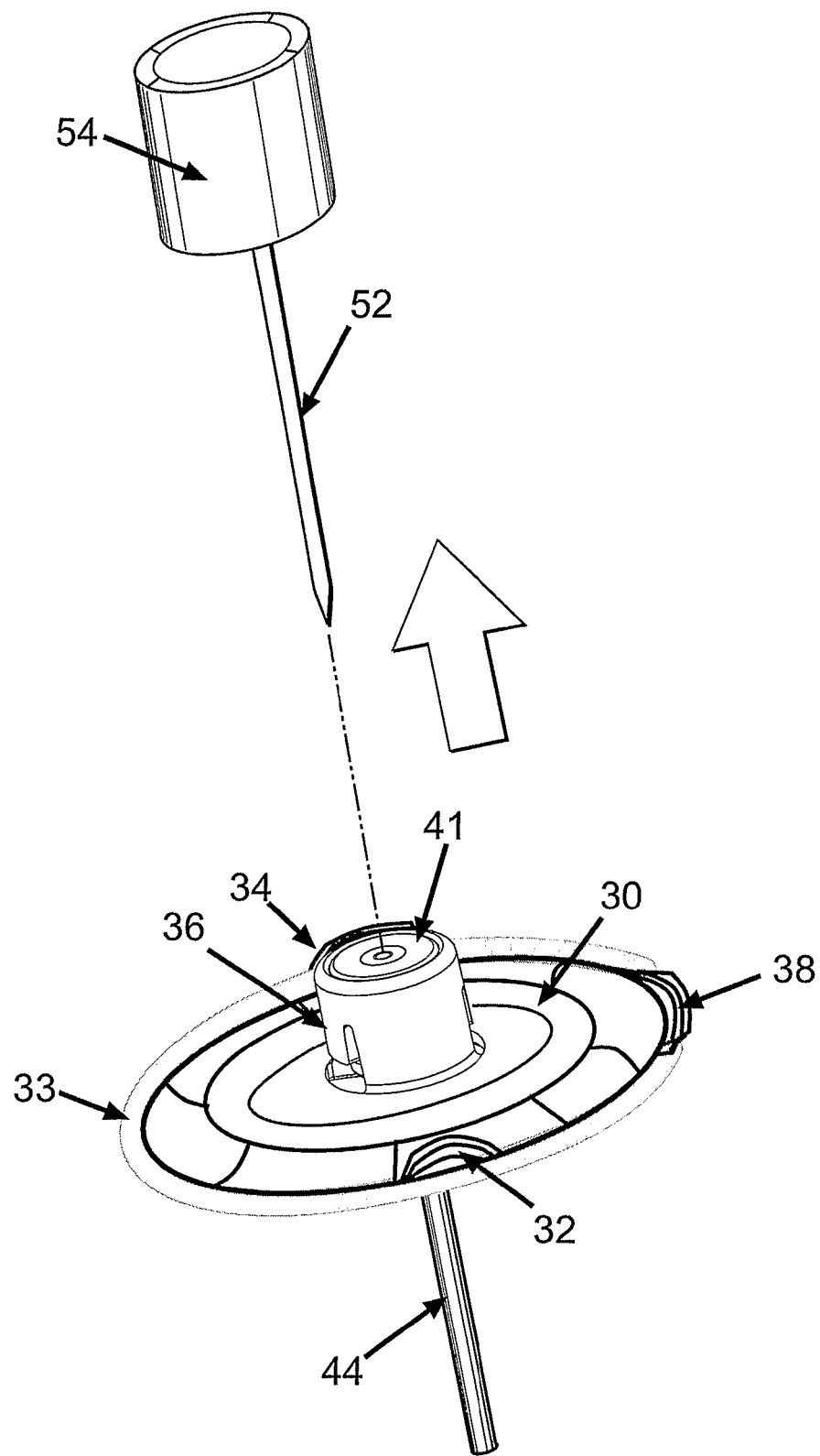
FIG. 3 is a perspective view of an exemplary housing with a cannula hub and a cannula connected thereto.

Referring to FIG. 3, a perspective view of a mounting housing 30 with a cannula hub 41 and a cannula 44 connected thereto after removal of the penetrating member 52 is shown.

Referring to FIGS. 4a-e, diagrams depicting manual securing of a housing and cannula insertion are shown. Particularly, in some embodiments, manual adherence of a mounting housing 30 to a user's skin 5 precedes the manual insertion of a cannula 44 into the body. In some embodiments, the user first attaches the mounting housing 30 to the skin 5 and then manually inserts the cannula 44 using a penetrating member 52 that includes a grip portion 54 at its blunt end. The attachment of the mounting housing 30 and the insertion of the cannula 44 may be performed substantially simultaneously in a single downwardly motion.

Figure 4A:
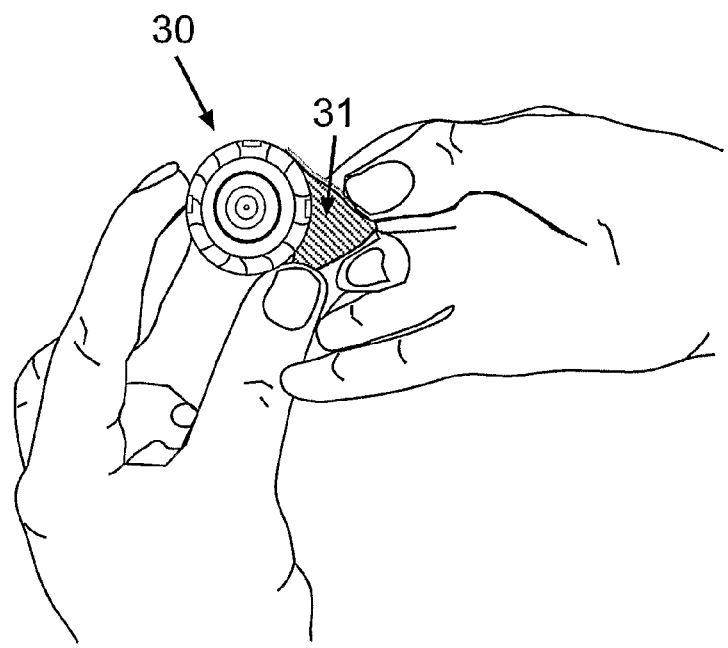
FIGS. 4a-e are views illustrating manual securing of a housing, and cannula insertion.
Figure 4B:
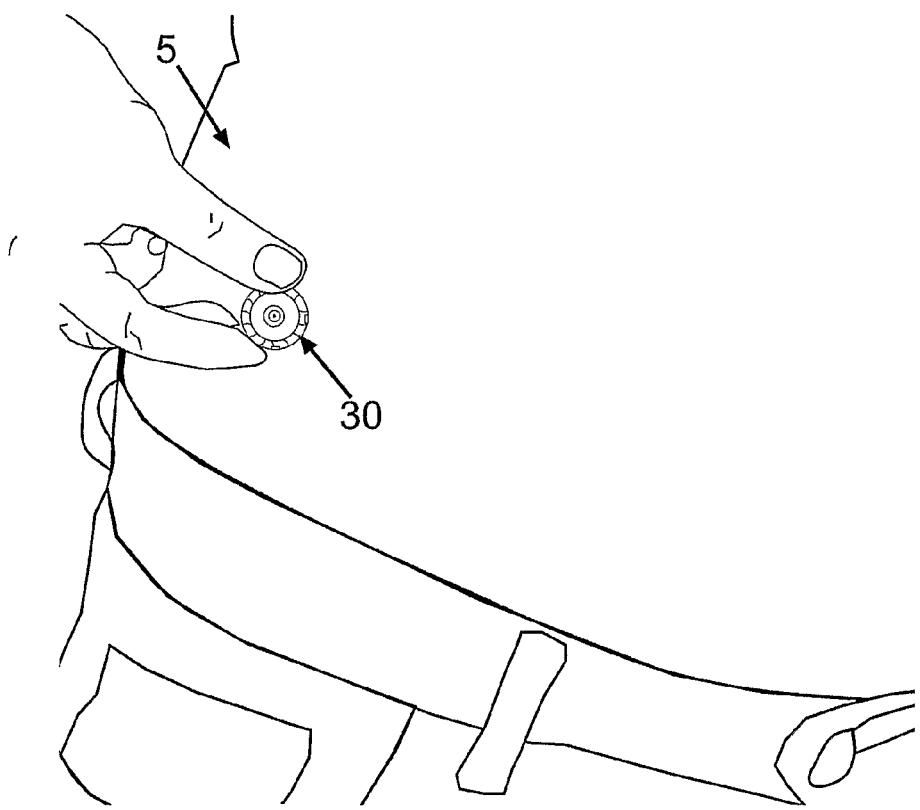
Figure 4C:
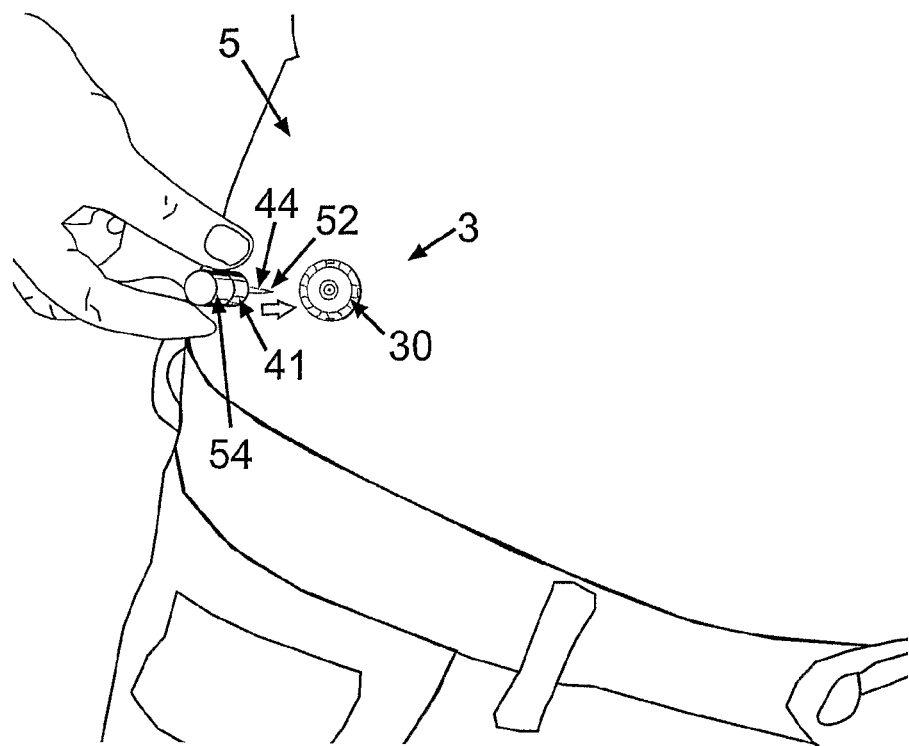
Figure 4D:
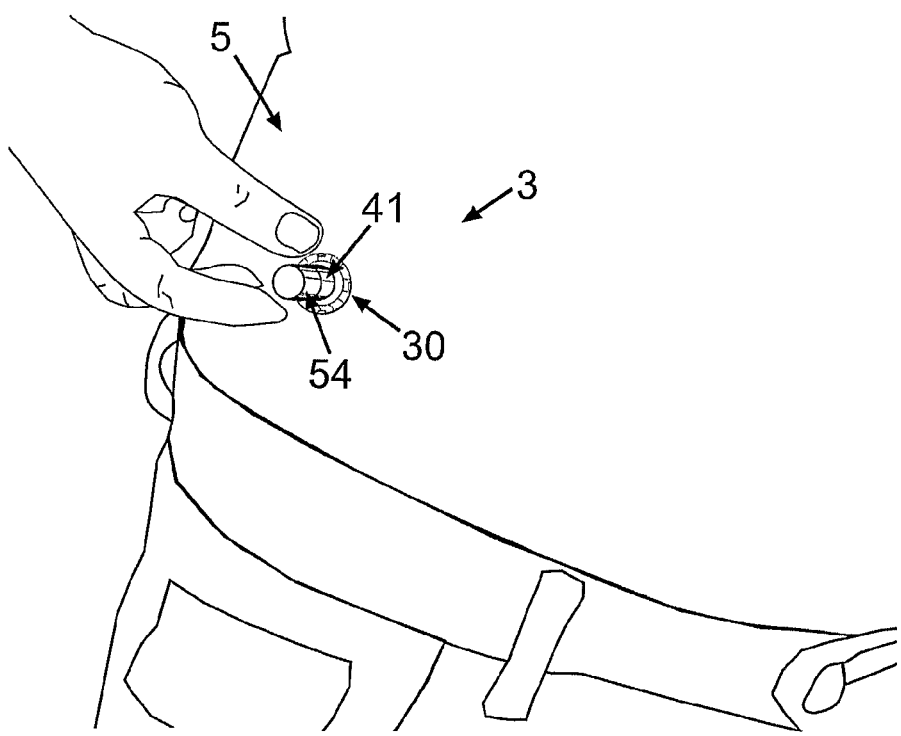
Figure 4E:
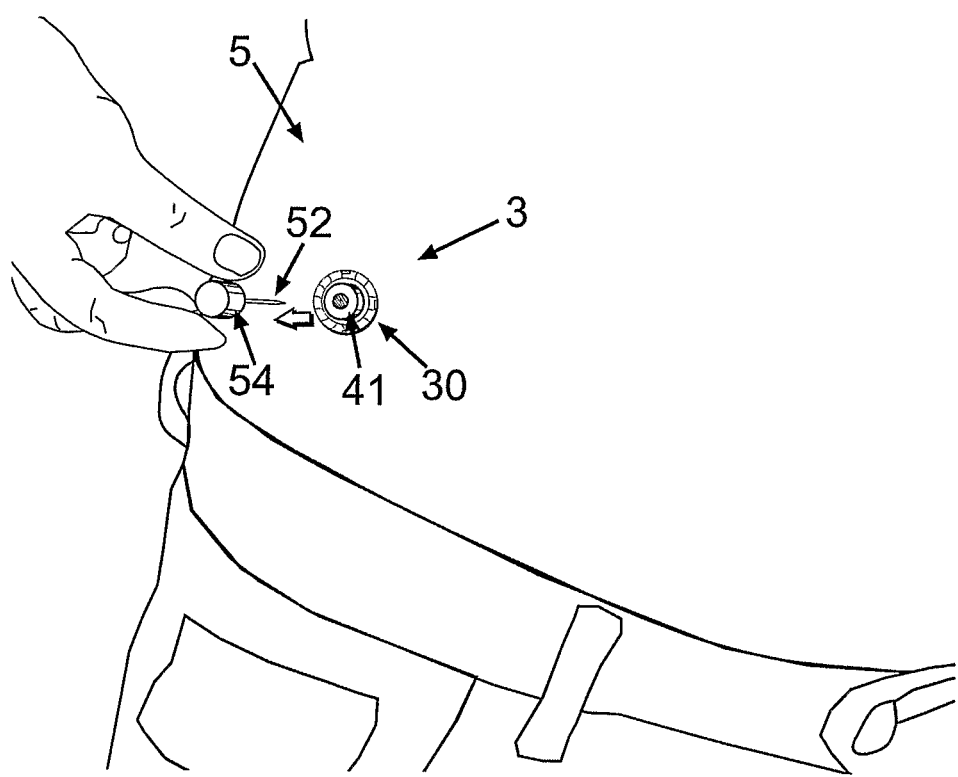

FIG. 4a shows removal of a protective paper 31 from the adhesive tape on the contact surface of the mounting housing 30. FIG. 4b shows securing (e.g., adherence) of the housing 30 to the skin 5. FIGS. 4c-d show manual insertion of the cannula 44 through the mounting housing's passageway 36 using the penetrating member 52. FIG. 4e depicts retraction of the penetrating member 52. The cannula (not shown in FIGS. 4a-e) remains in the subcutaneous tissue, and the cannula hub 41 may be secured to the mounting housing 30 by one or more anchors (not shown in FIGS. 4a-e).

Referring to FIGS. 5a-7e, diagrams and views depicting automatic cannula insertion with the aid of a preloaded insertion device (hereinafter "inserter") 50 are shown. In some embodiments, the mounting housing 30 may be first adhered to the skin 5 and the cannula 44 may then be automatically inserted through the secured mounting housing 30. In some embodiments, the mounting housing 30 and cannula 40 are both loaded into the inserter 50. The user first uses the inserter 50 to attach the mounting housing 30 to the skin 5 and then the cannula 40 may be automatically fired from the preloaded inserter 50.

Figure 5A:
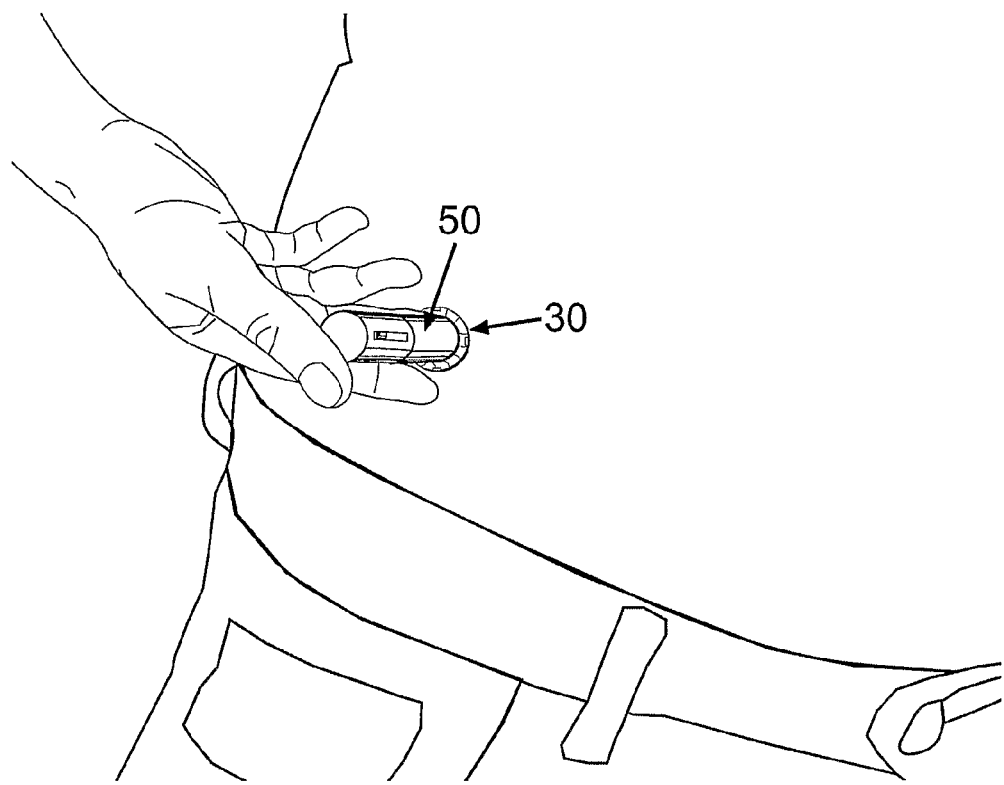
FIGS. 5a-b are views illustrating a secured housing and cannula insertion using an insertion device ("inserter").
Figure 5B:
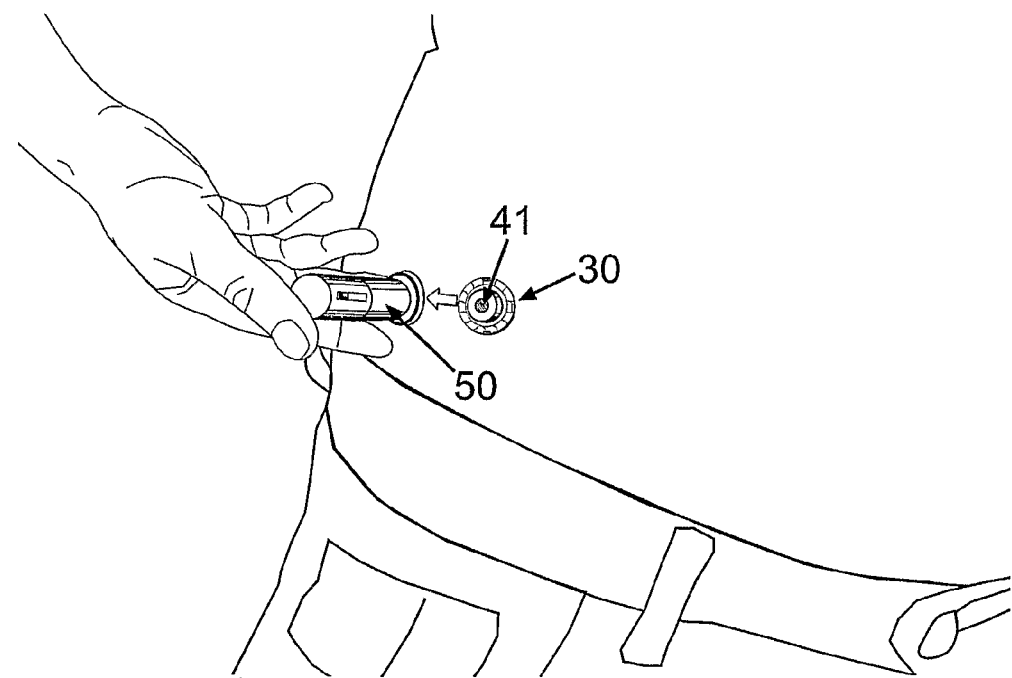

FIGS. 5a-b depicts the mounting housing 30 secured to the skin and the cannula inserted using an inserter 50. Further description of inserters such as the inserter 50 are described, for example, in co-owned U.S. Provisional Application No. 60/937,214, filed Jun. 25, 2007, the content of which is incorporated herein by reference in its entirety.

Referring to FIG. 5a, a diagram showing the inserter 50 placed proximate to the skin 5 is shown. The mounting housing 30 may be mounted on the inserter's 50 bottom side, and may be secured to the skin 5, at which point the user may initiate automatic cannula insertion using the preloaded inserter 50. FIG. 5b depicts the mounting housing 30 secured (e.g., adhered) to the skin after removal of the inserter 50. The cannula (not shown in FIGS. 5a-b) remains in the subcutaneous tissue, and the cannula hub 41 may be secured to the mounting housing 30 using one or more anchors (not shown in FIGS. 5a-b).

Referring to FIGS. 6a-f, schematic diagrams depicting an exemplary cannula insertion process using an inserter 50 are shown. The insertion process may be semi-automatic (e.g., automatic insertion of the cannula 44 and manual retraction of the penetrating member 52) or fully-automatic (e.g., both cannula insertion and penetrating member retraction are performed automatically).

Figure 6A:
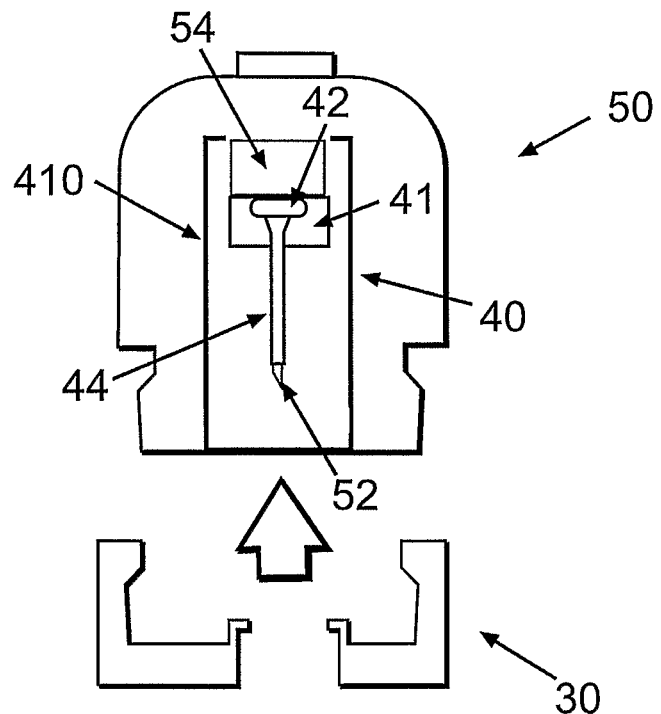
FIGS. 6a-f are schematic diagrams of an exemplary cannula insertion process using an inserter.
Figure 6B:
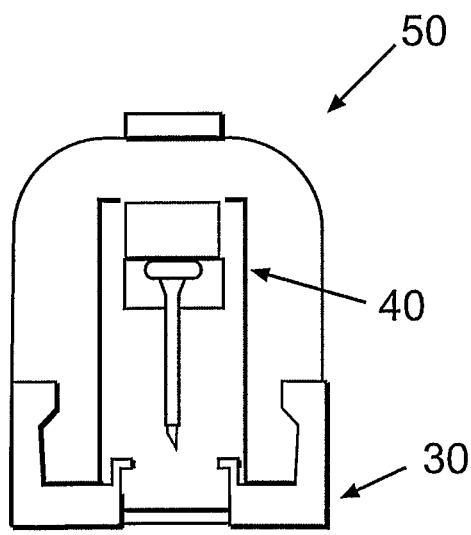
Figure 6C:
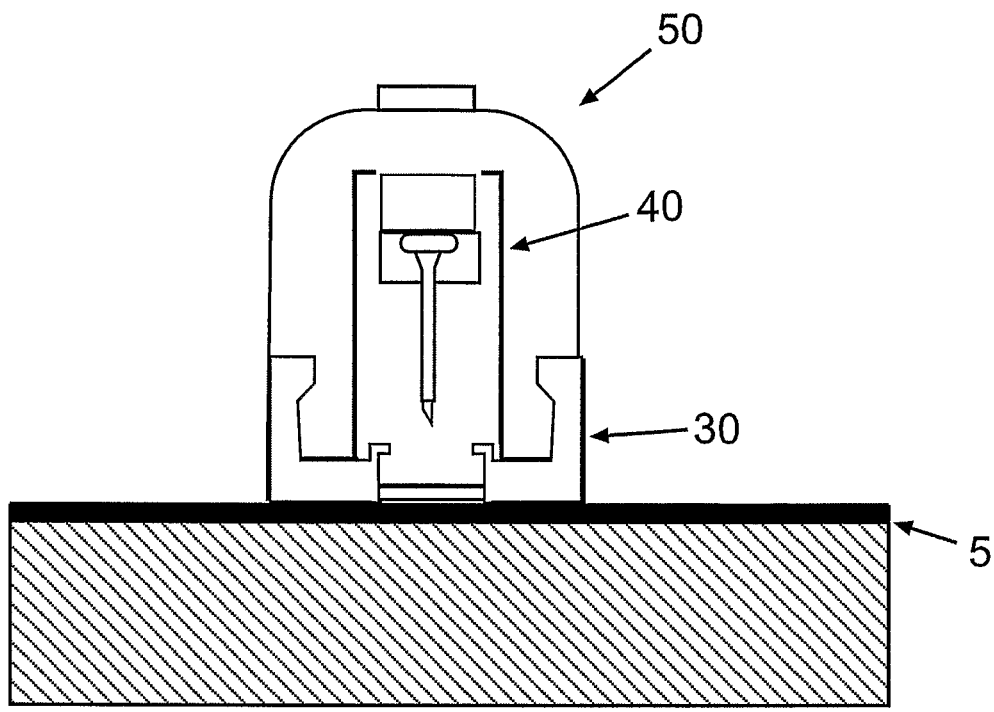
Figure 6D:
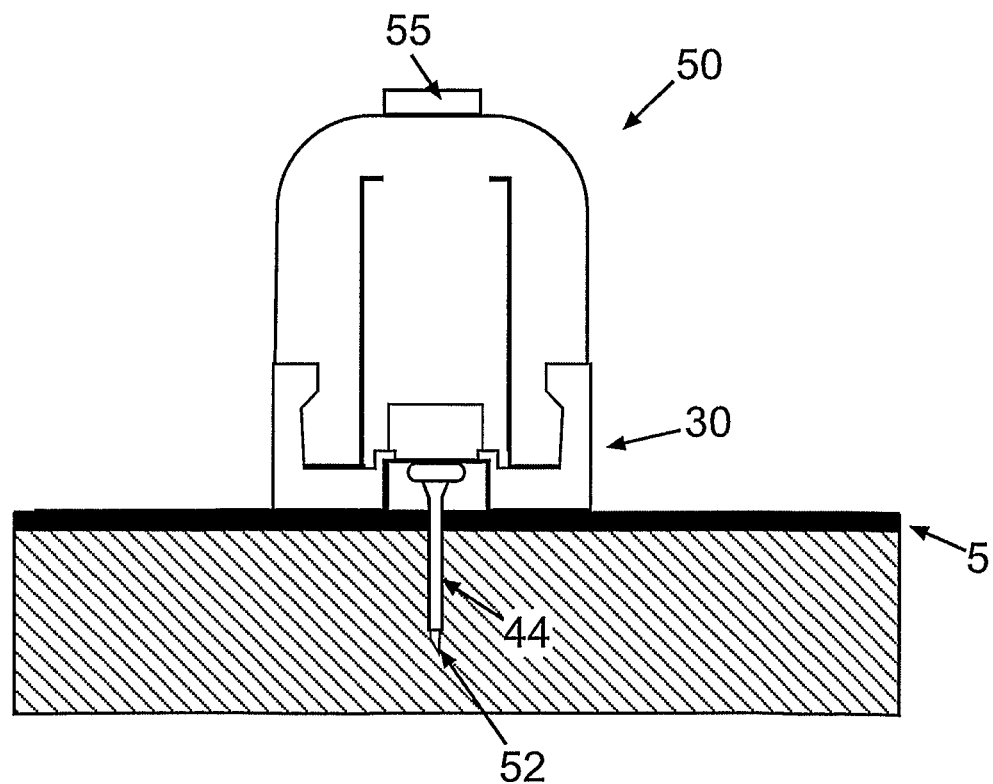
Figure 6E:
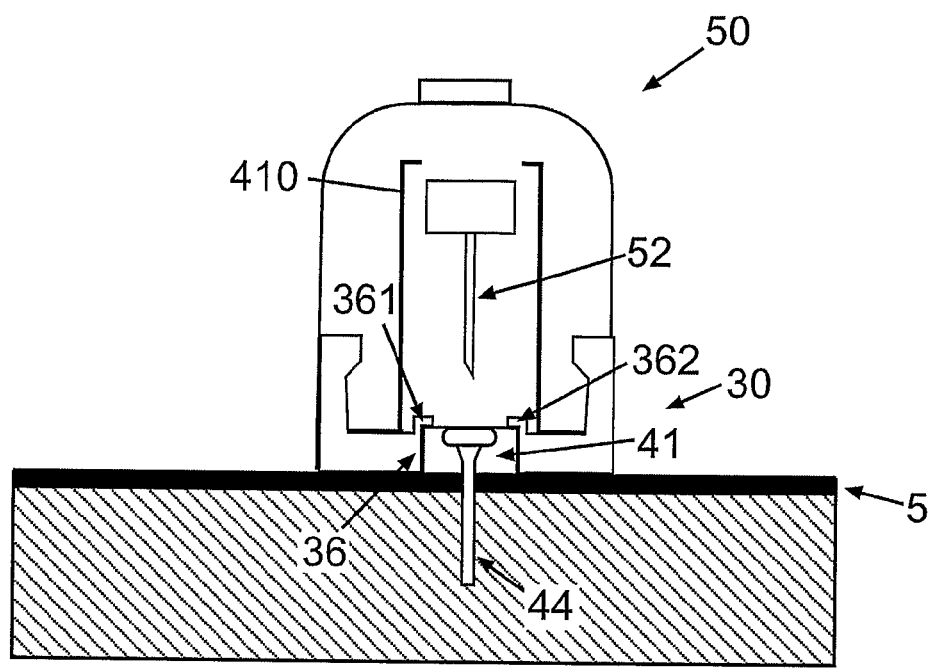
Figure 6F:
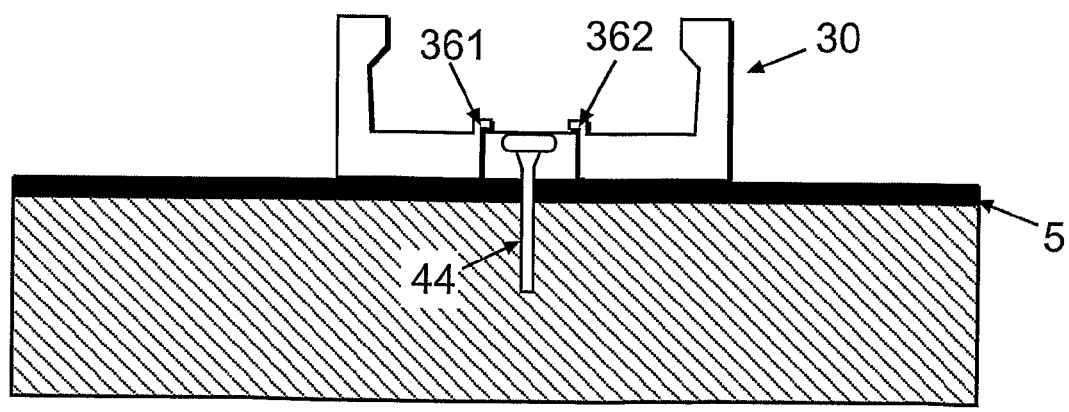

FIG. 6a shows connection of the mounting housing 30 to an inserter 50. In some embodiments, the inserter 50 may be preloaded with a cannula assembly 40, which may include one or more of the following components: a protector 410, a penetrating member 52 with a grip portion 54, a cannula 44 and a cannula hub 41 provided with a septum 42. In such embodiments, the protector 410 guards and encloses the penetrating member 52 and the cannula 44, as described, for example, in co-owned U.S. Provisional Patent Application No. 60/937,155, filed Jun. 25, 2007, the content of which is incorporated herein by reference in its entirety. In some embodiments, the cannula 40 may be loaded into the inserter 50 after connecting the mounting housing 30 to the inserter 50. FIG. 6b shows the mounting housing 30 connected to an inserter 50. FIG. 6c shows the inserter 50 with the mounting housing 30 connected thereto and being placed on the skin 5 after removal of the protective sheet from the adhesive tape on the bottom side (i.e., the contact surface) of the mounting housing 30. FIG. 6d shows insertion of the cannula 44 into the body, which may be initiated by pressing a trigger button 55. When initially inserted, the penetrating member 52 may be still in the user's body, but may then be retracted, as depicted in FIG. 6e. Penetrating member 52 may be retracted from the user's body and back into the protector 410. The cannula hub 41 remains connected to the walls of the passageway 36 using the one or more anchors 361 and/or 362, and the cannula 44 remains in the subcutaneous compartment. FIG. 6f shows the mounting housing 30 adhered to the skin 5 after completion of the cannula insertion process and removal of the inserter.

Automatic cannula insertion using an inserter 50 loadable with a cannula assembly 40 is advantageous for the following reasons:

a) Unintentional Pricking—The penetrating member 52 is enclosed (and thus concealed from view) within the protector 410 and thus the user is protected from unintentional pricking. Furthermore, the fact that the penetrating member 52 is not visible to the user during the insertion process constitutes an important psychological advantage over existing devices which require the user to insert the cannula 44 manually.

b) Reduced Pain—Hypodermic cannula insertion is generally accompanied by pain induced by skin piercing. However, fast insertion of the cannula can reduce the pain. Because automatic insertion is significantly faster than manual insertion, automatic cannula insertion therefore involves less pain for the patient. Using an inserter 50, in some embodiments, enables the employment of various mechanisms/instruments to reduce the pain associated with cannula insertion (hereinafter, "pain reduction mechanisms"), as described, for example, in co-owned U.S. Provisional Patent Application No. 60/937,163, filed Jun. 25, 2007, the content of which is hereby incorporated by reference in its entirety.

c) Sterility—The protector 410, which is part of the cannula assembly 40, provides sterility because the user cannot touch the cannula 44.

Figures 7A, 7B:
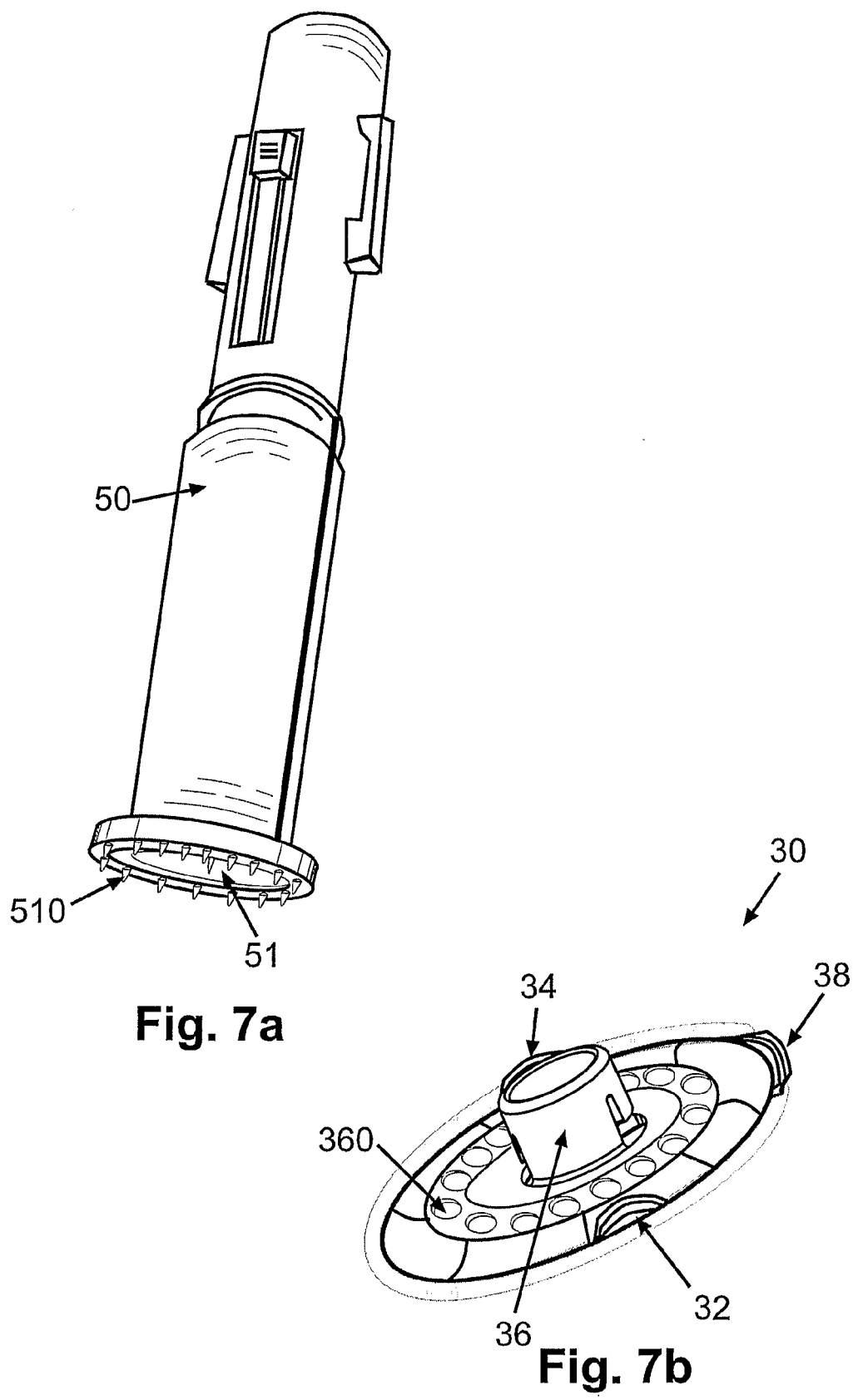
FIGS. 7a-e are views and diagrams of an exemplary inserter having an array of protrusions, connected to a mounting housing with complementary pores.
Figure 7C:
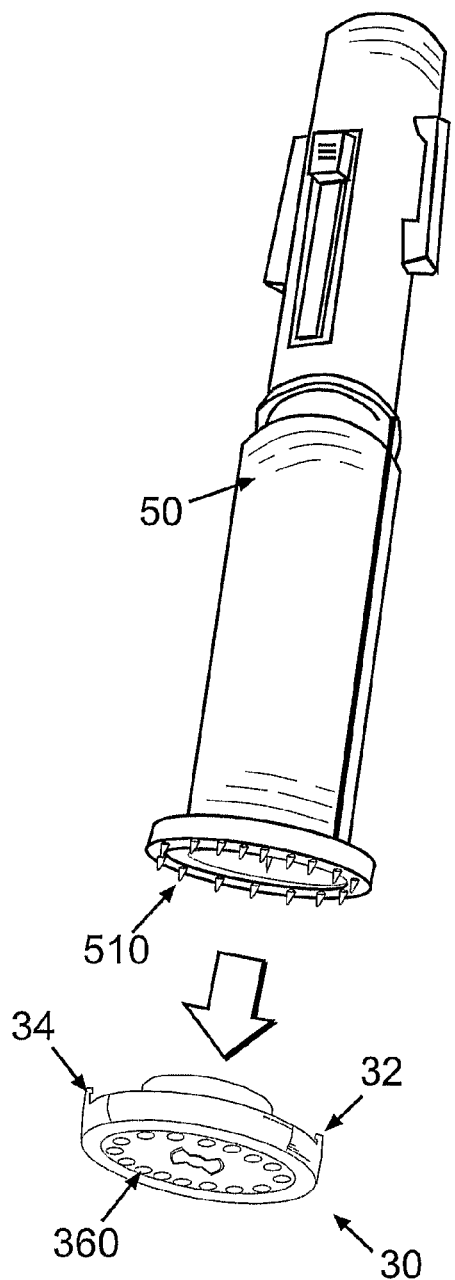
Figure 7D:
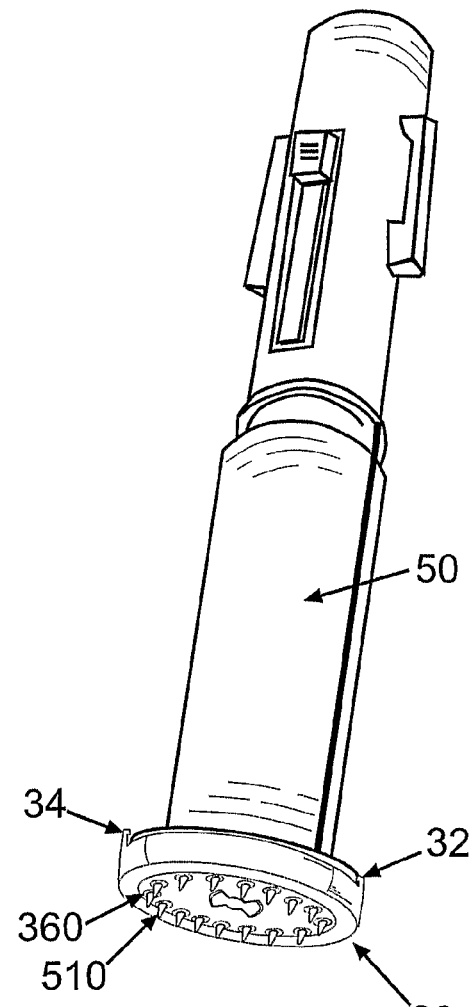
Figure 7E:
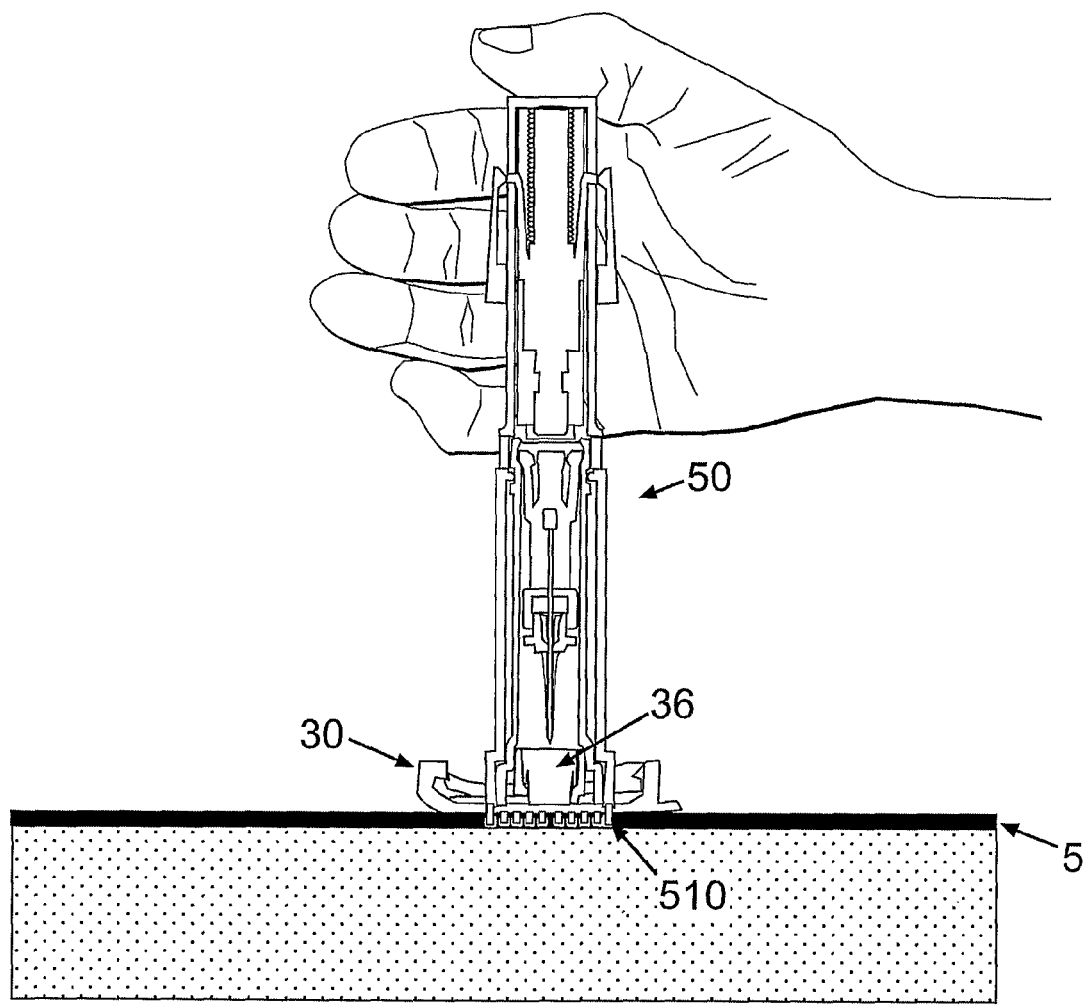

Referring to FIGS. 7a-e, diagrams of an exemplary pain reduction mechanism are shown. FIG. 7a shows an inserter 50 that includes an array of projections or protrusions 510 surrounding its bottom opening 51 and extending therefrom. The protrusions may be either blunt or sharp, or a combination thereof. FIG. 7b depicts a mounting housing 30 provided with pores 360 surrounding the passageway 36. The pores 360 may be configured and dimensioned to receive the inserter's protrusions 510 upon connection of the mounting housing 30 to the inserter 50. FIG. 7c shows the inserter 50 and the mounting housing 30 before connection of the two. FIG. 7d shows the inserter 50 and the mounting housing 30 connected to each other. The inserter's protrusions 510 are, in some embodiments, aligned with the mounting housing's pores 360. FIG. 7e is a cross-sectional view of the inserter 50 connected to the mounting housing 30, after securing of the mounting housing to the skin 5. Prior to cannula insertion, the user applies force on the inserter 50, which in turn applies pressure onto the skin surrounding the passageway 36 via the protrusions 510 which are received through the pores defined on the mounting housing 30 thus reducing the pain sensation associated with skin piercing during cannula insertion. A cannula insertion process using the depicted inserter 50 is further described, for example, in co-owned U.S. Patent Applications Nos. 60/937,163, 60/937,155 and 60/937,214, all filed on Jun. 25, 2007, the contents of all of which are hereby incorporated by reference in their entireties.

In some embodiments, the user may control (e.g., select) the desired cannula penetration angle, whether the insertion process is performed manually or automatically, using, for example, a dedicated inserter. Referring to FIGS. 8-9, diagrams and views of exemplary angled cannula insertions are shown.

Figure 8A:
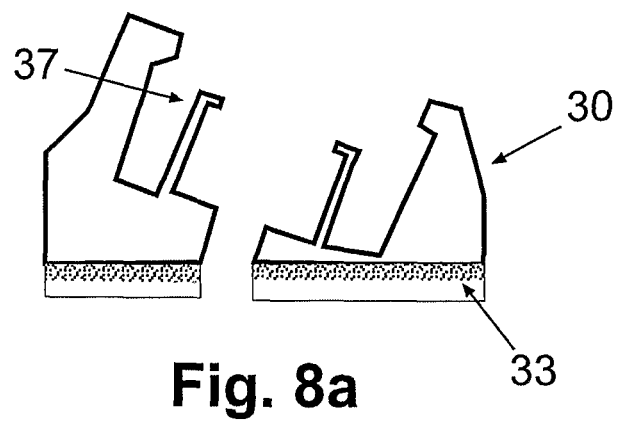
FIGS. 8a-d are schematic diagrams of an exemplary housing with a slanted well configured to facilitate insertion of a cannula through the slanted well.
Figure 8B:
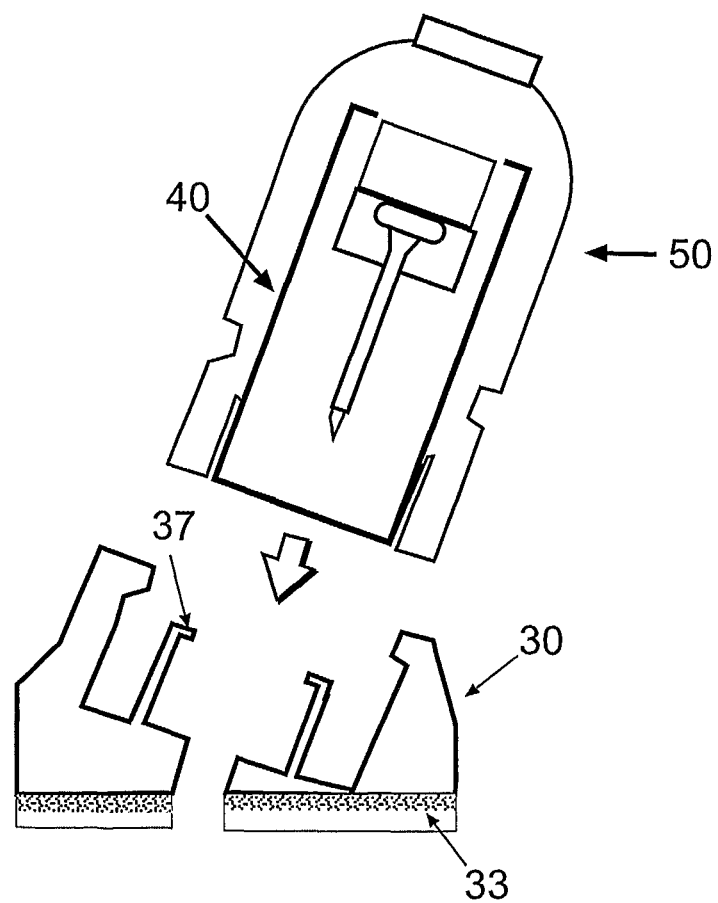
Figure 8C:
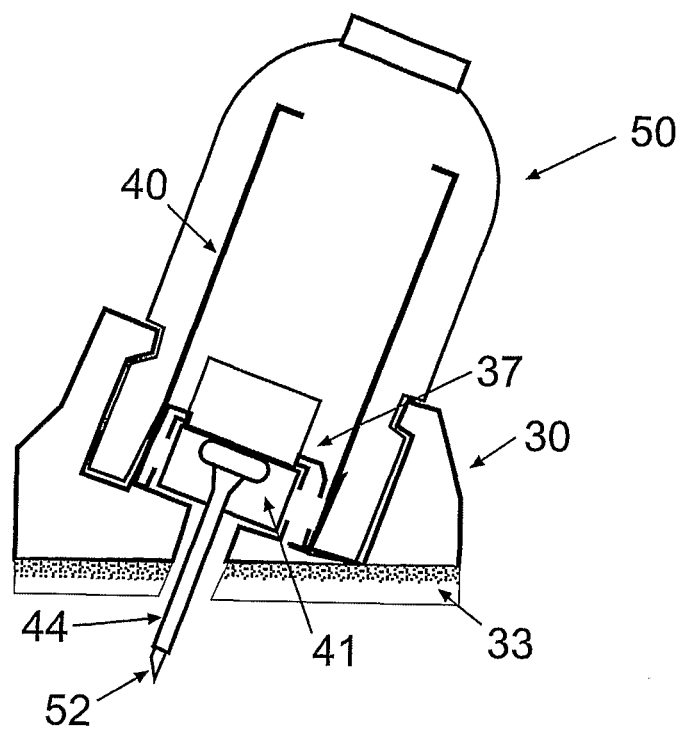
Figure 8D:
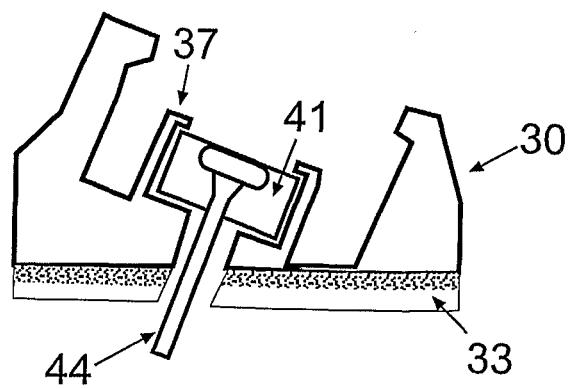

FIG. 8a is a schematic diagram of an exemplary mounting housing 30 with a slanted well 37 defining a slanted (angled) passageway to receive a cannula such that the cannula forms an angle other than 90° with respect to the surface of the skin. That is, the passageway is slanted with respect to the bottom side of the mounting housing 30. FIG. 8b shows an inserter 50 before connection to the mounting housing 30 having the slanted well 37. FIG. 8c shows the inserter 50 connected to the mounting housing 30 after insertion of the cannula 44 with the penetrating member 52. FIG. 8d shows the mounting housing 30 in a mating configuration (i.e., in an assembled configuration) with the cannula hub 41 and the cannula 44 connected thereto after cannula insertion and removal of the inserter 50.

In some embodiments, the mounting housing 30 may include a tiltable well to define a slanted passageway with an adjustable angle. Referring to FIG. 9a, a perspective view of an exemplary mounting housing 30 provided with a tiltable well 37, to enable the user to adjust the desired cannula penetration angle is shown. In some embodiments, the tiltable well 37 may include a tilting mechanism. For example, the tilting mechanism may be attached to the mounting housing's base 300 using, for example, one or more rods 35 and 35', which are each provided with a gear (e.g., cogwheel) 39 and 39' at their respective distal ends. The rotateable gears 39 and 39' are located within dedicated grooves 390 and 390' in the housing's base 300. Each groove 390 and 390' may be configured such that it includes a wide section to enable rotation of the gears 39 and 39' within the respective grooves 390 and 390' and a narrow section into which the respective gear is placed to lock the gear into place. The narrow section (which may be positioned as the bottom part of the groove) may be shaped to precisely fit the shape of the gear 39 and 39'. This configuration enables tilting of the well 37 to a desired angle, and then pushing the well 37 towards the skin of the patients (e.g., in a generally vertical downwards direction, wherein the vertical pushing direction is with respect to the mounting housing's base 300) until the gears 39 and 39' are received in the narrow sections of the grooves 390 and 390'. The configuration of the narrow section of each groove 390 and 390' prevents the respective gear from rotating and from being dislodged and moving back to the wide sections of the respective groove after being caught in the narrow section. This ensures that the well 37 may be fixed in the desired angle.

Figure 9D:
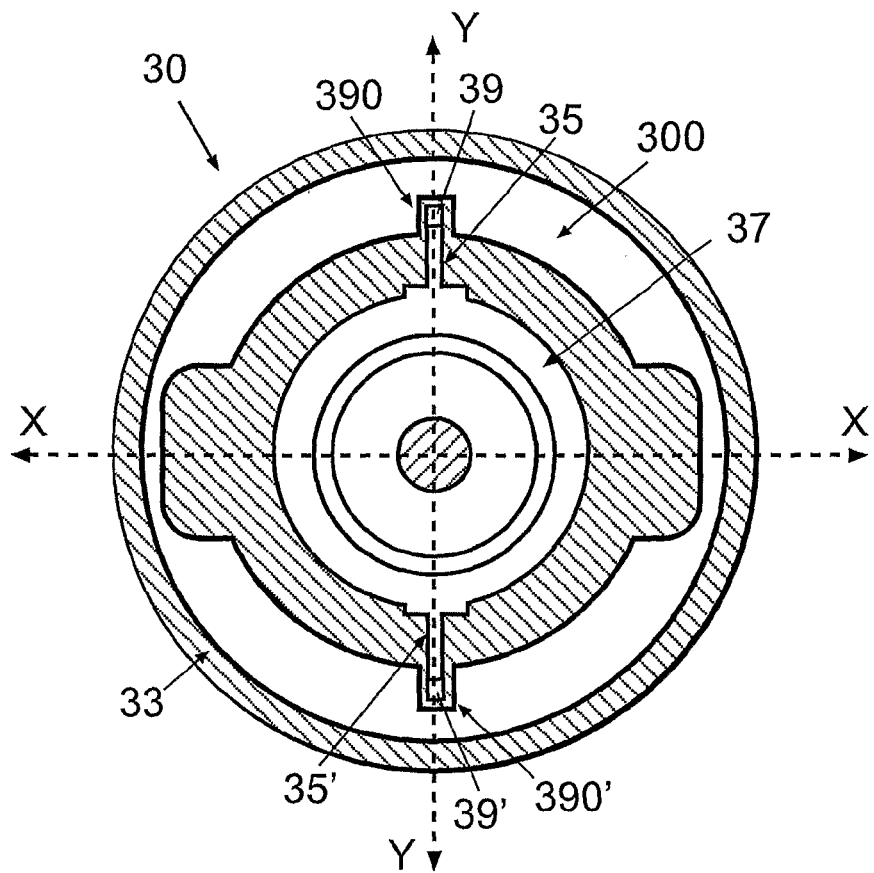
Figure 9E:
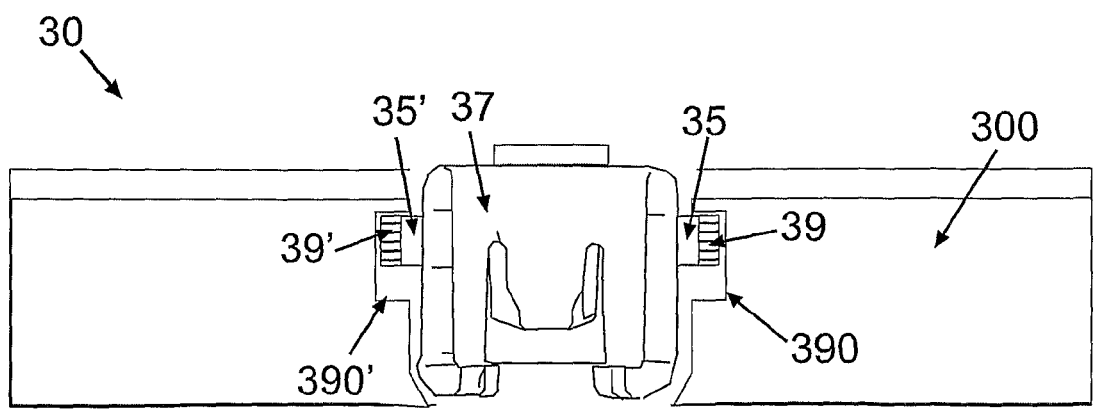

FIG. 9b is an enlarged schematic diagram of an exemplary groove 390 and a gear 39 within it prior to setting an insertion angle with the tiling mechanism. As shown, the gear 39 is located in the wide section of the groove 390 (the upper part of the groove, as shown in the figure) and can rotate freely. FIG. 9c shows the groove 390 and the respective gear 39 after setting an insertion angle. The well with the associated rods and gears may be pushed down (in an up-down orientation of the mounting housing), and the gears are retained in the narrow (e.g., lower) section of the grooves (e.g., the groove designated by numeral 390). FIG. 9d shows a top view of the tiltable well 37. FIG. 9e shows a cross-sectional view of the tiltable well 37 taken along the central axis YY designated in FIG. 9d.

Referring to FIGS. 9f-h, cross-sectional diagrams of the tiltable well 37 taken along the central axis XX designated in FIG. 9d are shown. The schematics depict how the tiltable well 37 can be tilted to a desired angle. After setting the desired insertion angle, a cannula 40 (i.e., the cannula structure or assembly) can be inserted through the well 37.

Figure 9I:
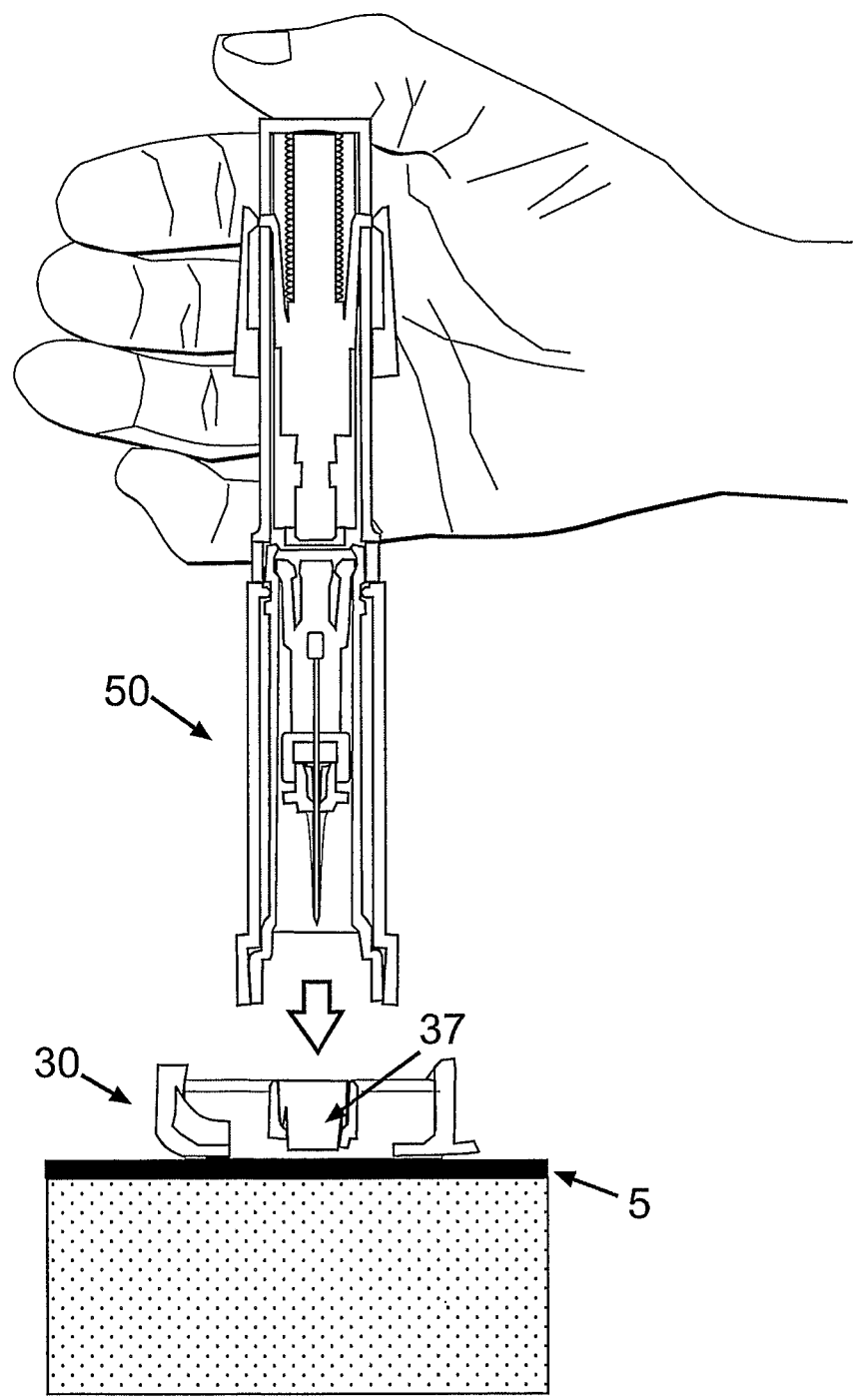
Figure 9J:
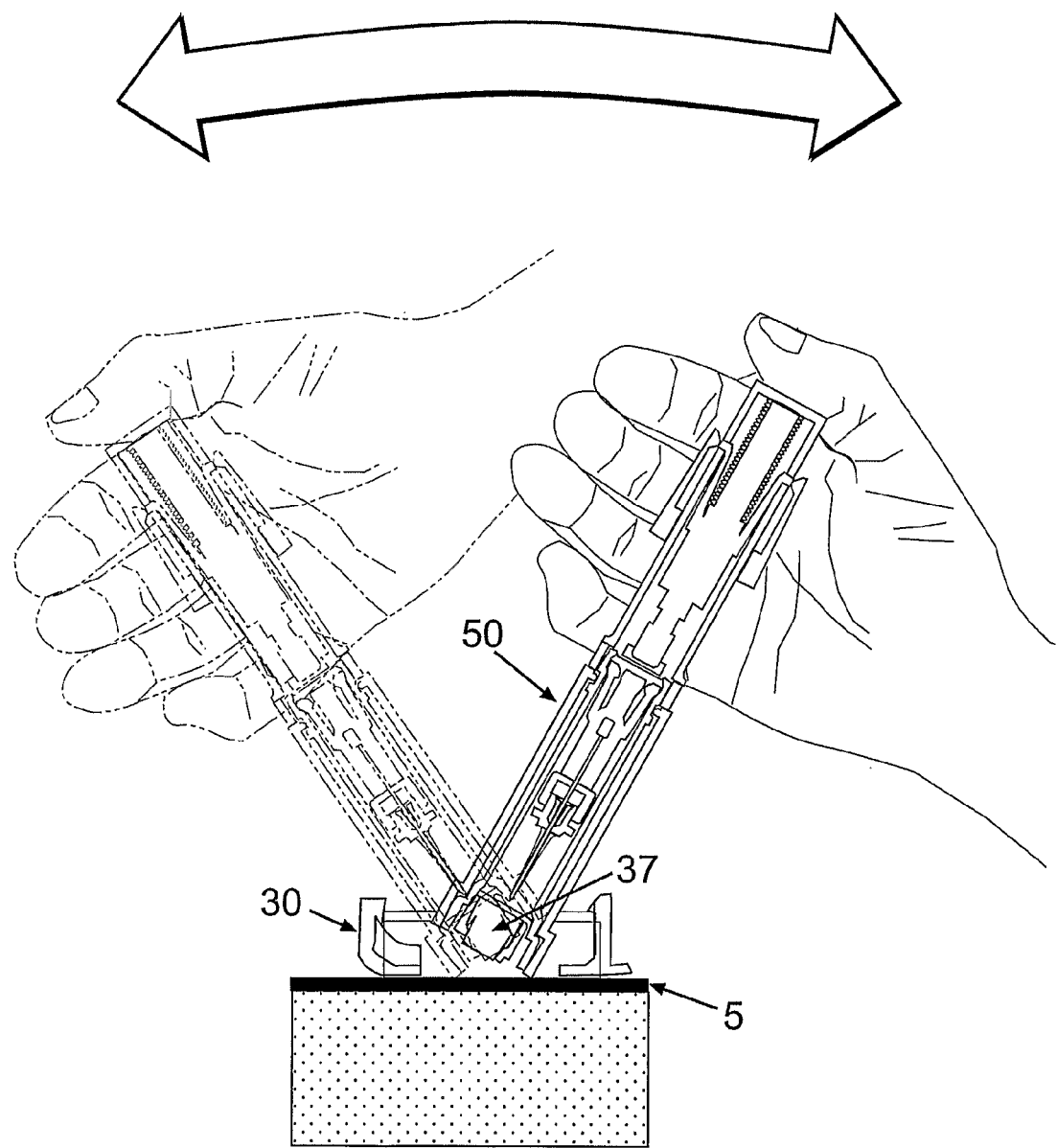

FIG. 9i shows a cross-sectional view depicting an inserter 50 connected to the mounting housing 30. In some embodiments, the inserter 50 may be connected directly to the well 37 and may be used for tilting the well 37 to the desired insertion angle before initiating cannula insertion, as shown, for example, in FIG. 9j. That is, the inserter can be use as a type of lever to apply torque to the tiltable well to tilt it to the desired angle. The inserter, under these circumstances, also performs insertion operation to insert the cannula 40.

After securing of the mounting housing 30 to the patient's skin 5 and inserting a cannula 44 into the body, a portable therapeutic device (be it a fluid delivery device or a sensing device) 1 may be coupled to the mounting housing 30.

Figure 10A:
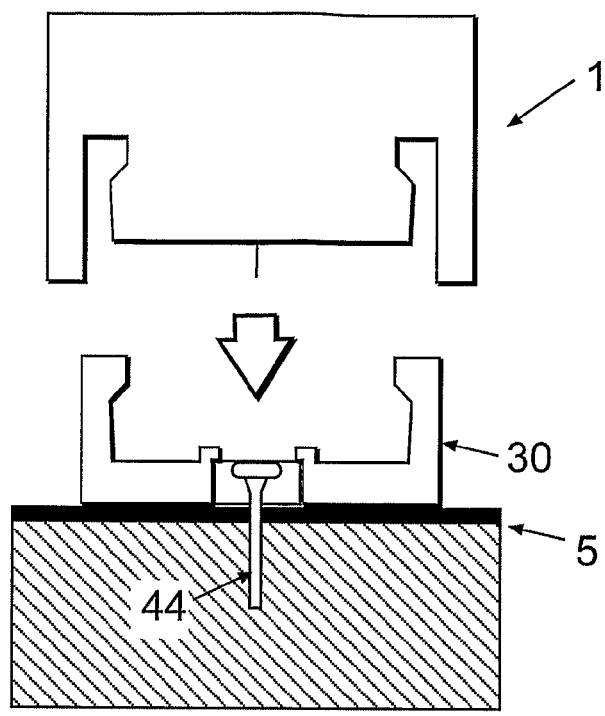
FIG. 10a is a schematic diagram of an exemplary housing connectable to a therapeutic device prior to connection of the two.
Figure 10B:
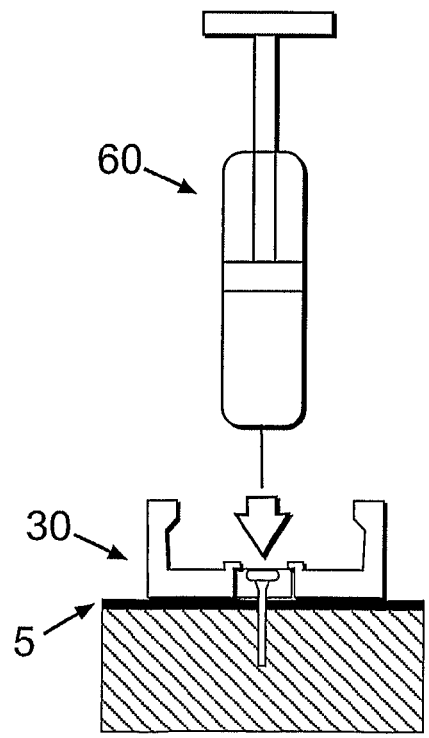
FIGS. 10b-g are schematic diagrams of various exemplary types of fluid delivery devices connectable to an exemplary mounting housing.
Figure 10C:
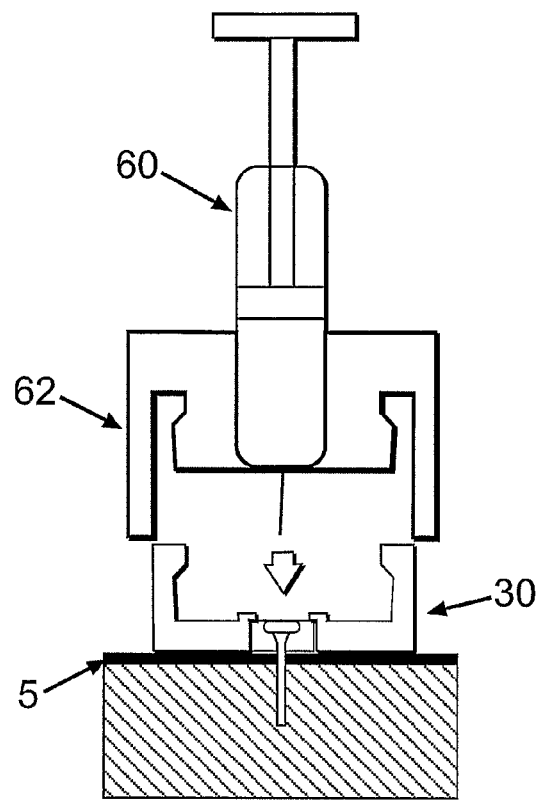
Figure 10D:
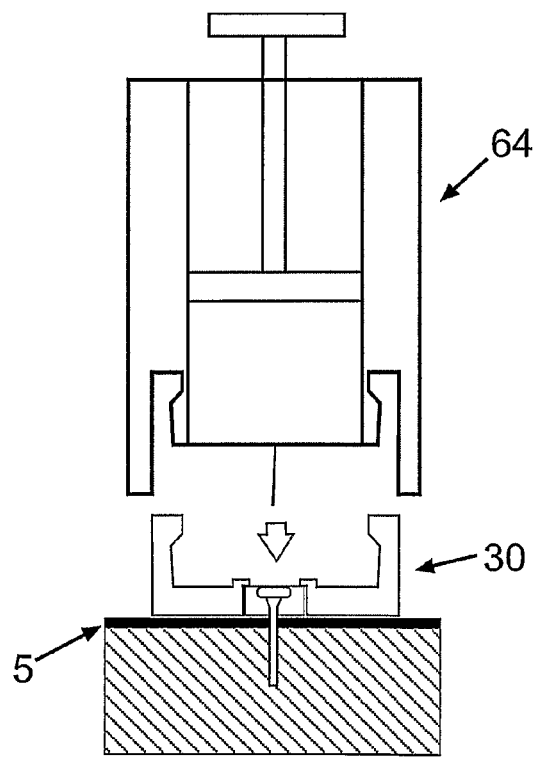
Figure 10E:
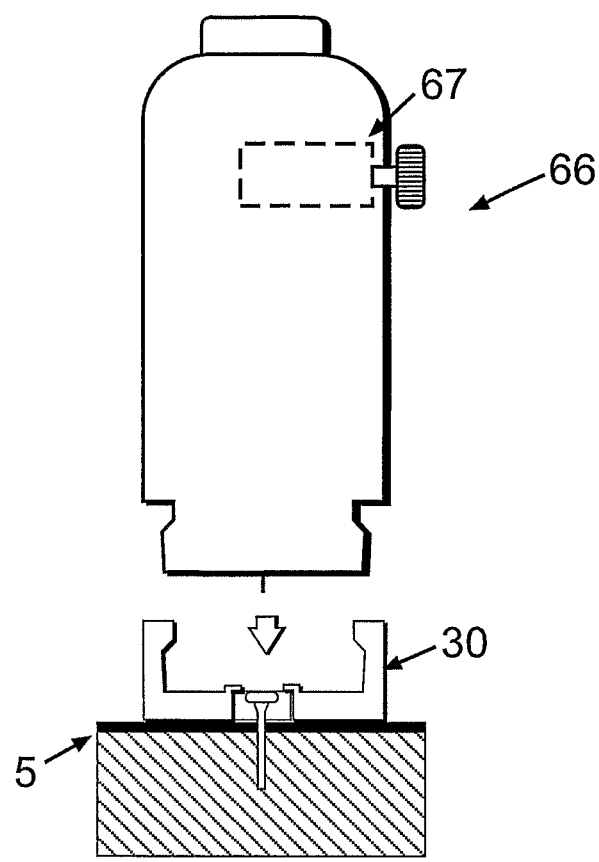
Figure 10F:
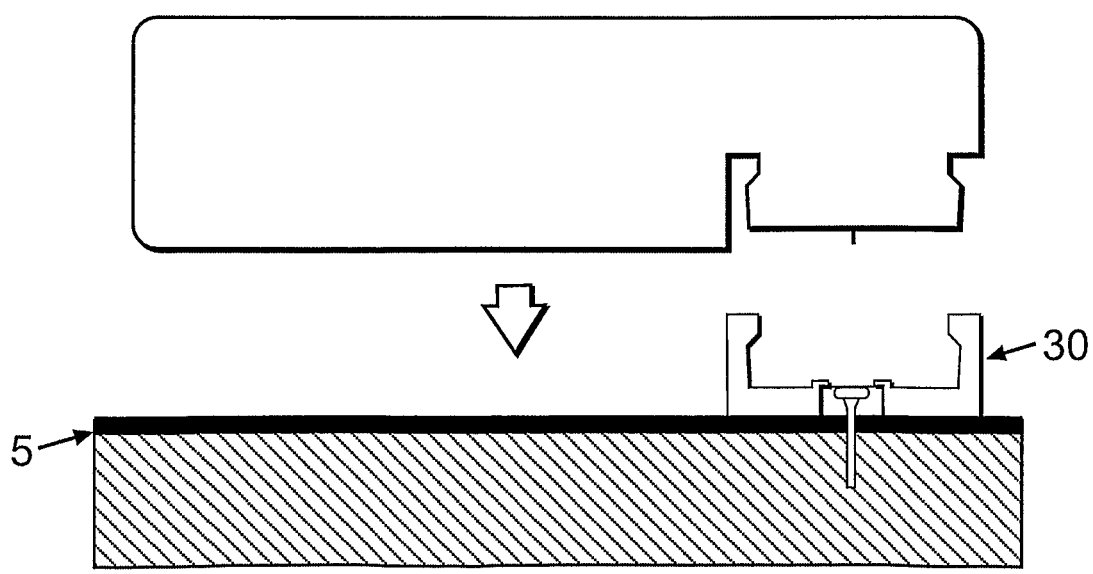
Figure 10G:
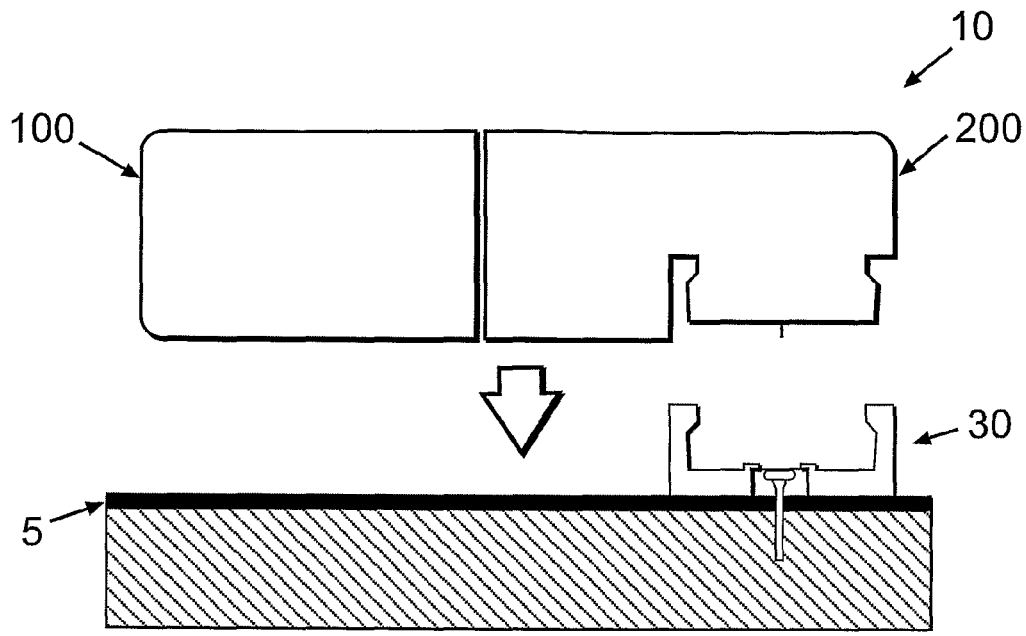

Referring to FIG. 10a, a schematic diagram of an exemplary mounting housing 30 connectable to a portable therapeutic device (e.g., fluid delivery device) 1 before connection is shown. Referring to FIGS. 10b-g, schematic diagrams of exemplary types of therapeutic devices that are connectable to the mounting housing 30 are shown. FIG. 10b is a schematic diagram showing a standard syringe 60. FIG. 10c shows a standard syringe 60 coupled to a dedicated adapter 62 that enables connection of the syringe 60 to the mounting housing 30. FIG. 10d shows a dedicated syringe 64. FIG. 10e shows a jet/pen 66 connectable to the housing 30, which may include a counter 67 to enable the user to electronically and/or mechanically preset the amount of fluid to be delivered. It will be noted that such a counter may be employed in all other described therapeutic devices. FIG. 10f is a schematic diagram of an exemplary single-part infusion pump 10 connectable to the housing 30. FIG. 10g shows an infusion pump 10 having two parts, e.g., a reusable part 100 and a disposable part 200. A description of an exemplary infusion pump 10 which may be connectable to the housing 30 is described in co-owned U.S. Provisional Patent Applications Nos. 60/963,071, filed on Aug. 1, 2007, and 61/003,169, entitled "A Device for Drug Delivery", filed on Nov. 14, 2007, the contents of both of which are hereby incorporated by reference in their entireties.

Figure 19A:
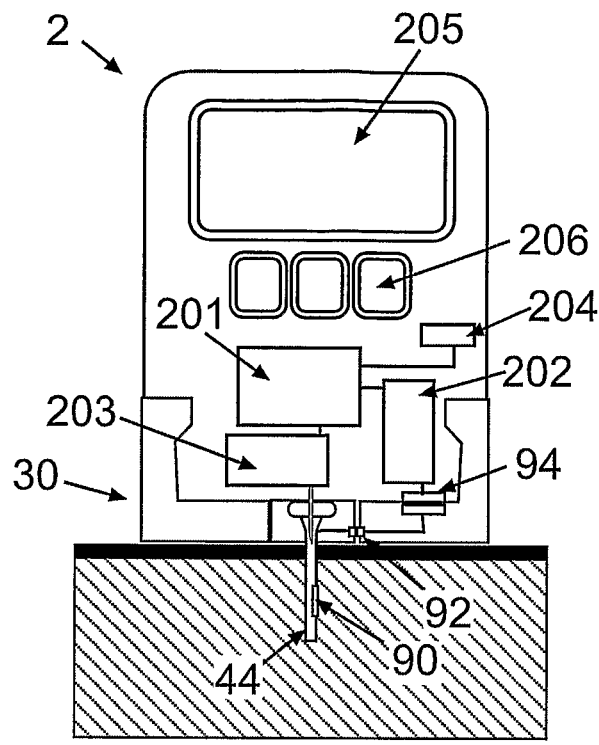
FIGS. 19a-c are schematic diagrams of an exemplary sensing device connected to a mounting housing.

It should be noted that a body analyte sensor, e.g., a blood glucose sensor, either as a stand-alone item or combined with an infusion pump 10, may also be connected to a mounting housing 30, as described, for example, below in relation to FIGS. 19a-c.

Figure 11A:
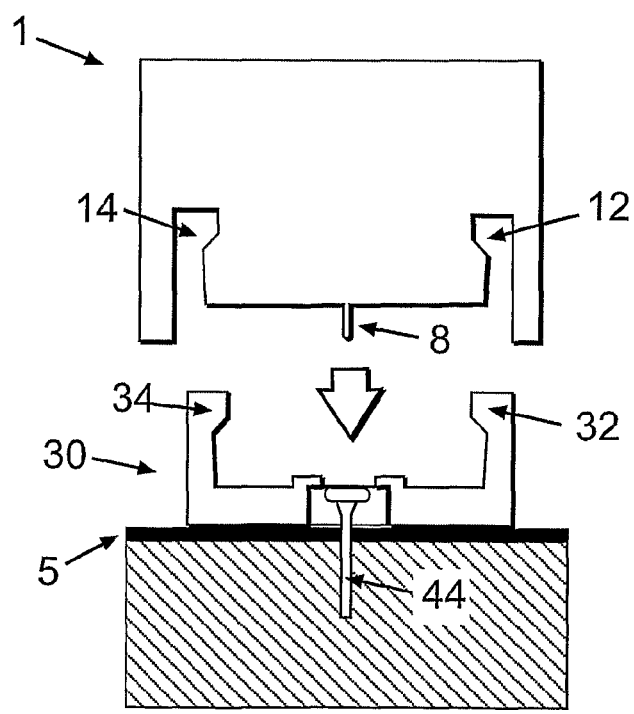
FIGS. 11a-c are schematic diagrams of several exemplary options for establishing a connection between a therapeutic device and a housing.
Figure 11B:
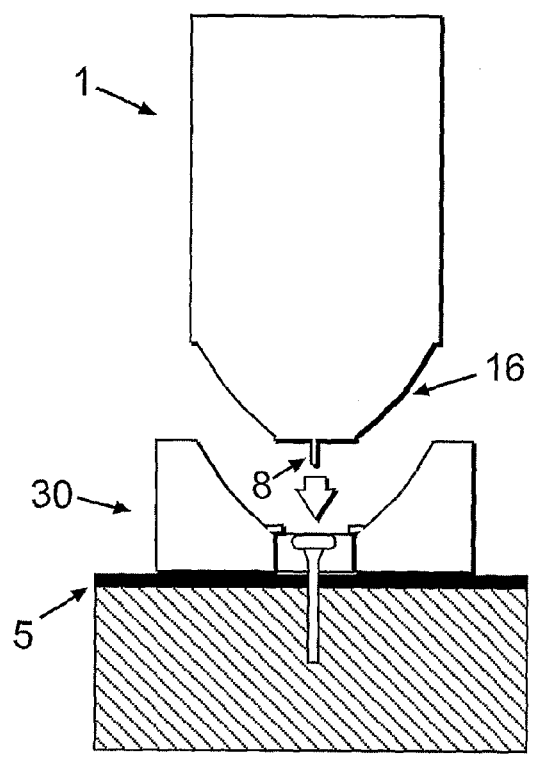
Figure 11C:
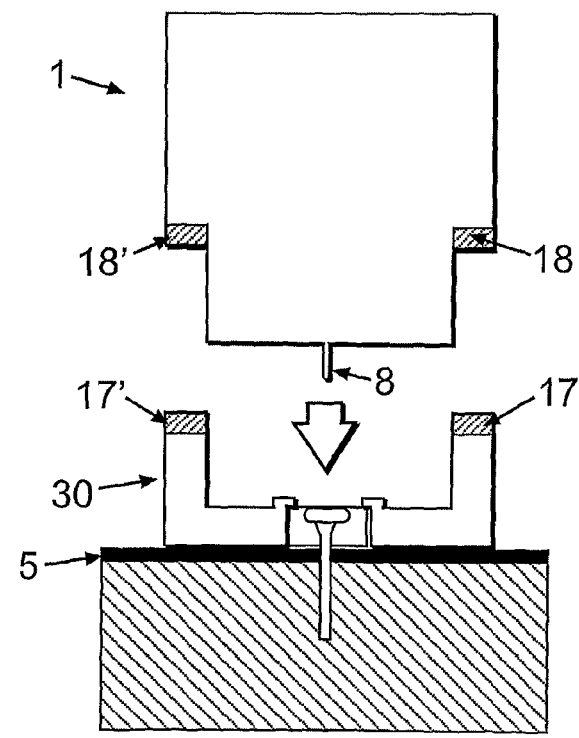

Referring to FIGS. 11a-c, schematic diagrams depicting several exemplary mechanisms for establishing a connection between a therapeutic device 1 (e.g., a delivery device, a sensing device, etc.) and the mounting housing 30, and ensuring that the delivery needle 8 is aligned with the cannula 44 are shown.

FIG. 11a shows a mounting housing 30 provided with latches 32 and 34. The connection between the delivery device 1 and the mounting housing 30 may be performed by engagement of the latches 32 and 34 with corresponding complementary recesses 12 and 14 defined in the therapeutic device 1. FIG. 11b shows a concave mounting housing 30 and a dedicated therapeutic device 1 with a convex bottom portion 16 that fits within the concave housing 30. FIG. 11c shows a mounting housing 30 provided with one or more magnets 17 and 17' and a therapeutic device 1 provided with corresponding one or metal plates 18 and 18' configured to be magnetically coupled to the one or more magnets. In some embodiments, the therapeutic device 1 may be provided with the magnets and the housing 30 may be provided with the metal plate(s). When the therapeutic device 1 is brought in close proximity to the mounting housing 30 the one or more metal plates 18 and 18' attract the magnets 17 and 17' and thus proper alignment and connection may be established.

Referring to FIGS. 12a-g, diagrams depicting an exemplary device and method for drawing fluid from a vial and filling a syringe 60 using an adapter 62 that is also used to align the syringe needle and the cannula 44 are shown.

Figure 12A:
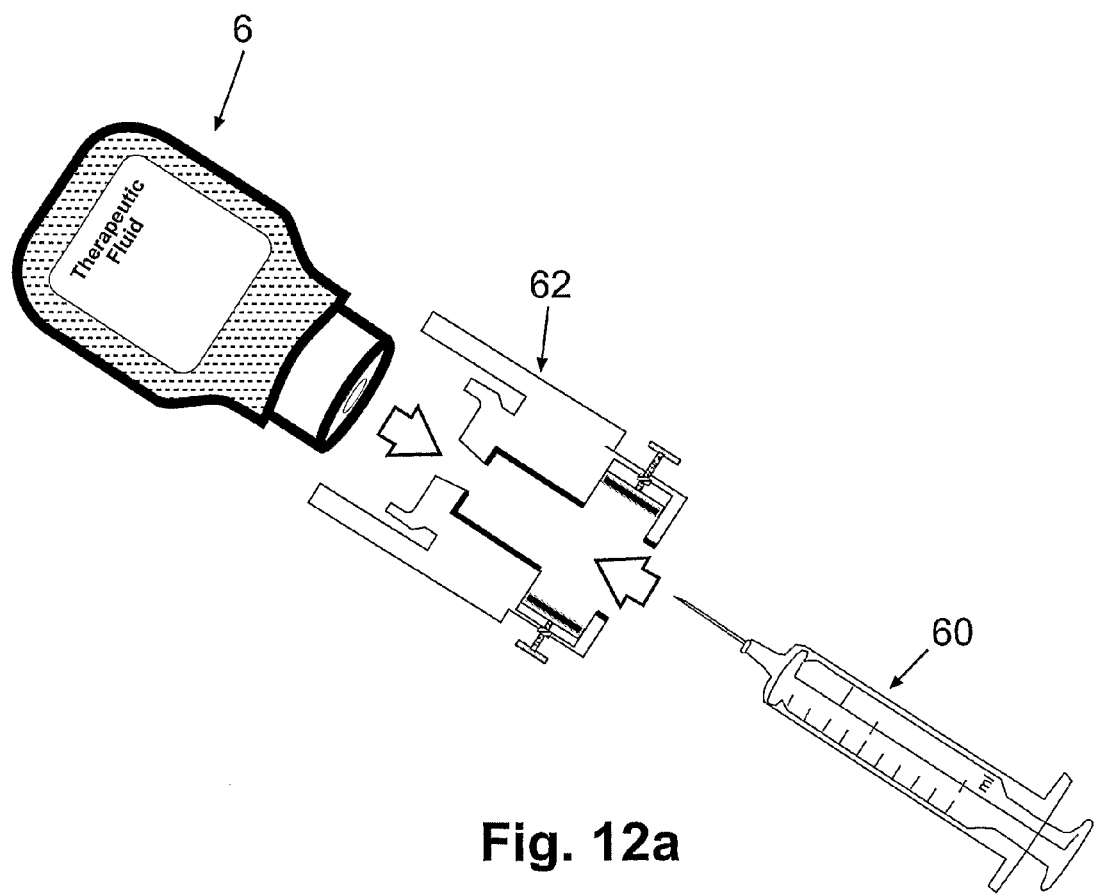
FIGS. 12a-g are views and diagrams of an exemplary device and an exemplary procedure for drawing fluid from a vial into a syringe using an adapter, which may be then connected to a mounting housing to facilitate alignment of the syringe needle and the cannula.
Figure 12B:
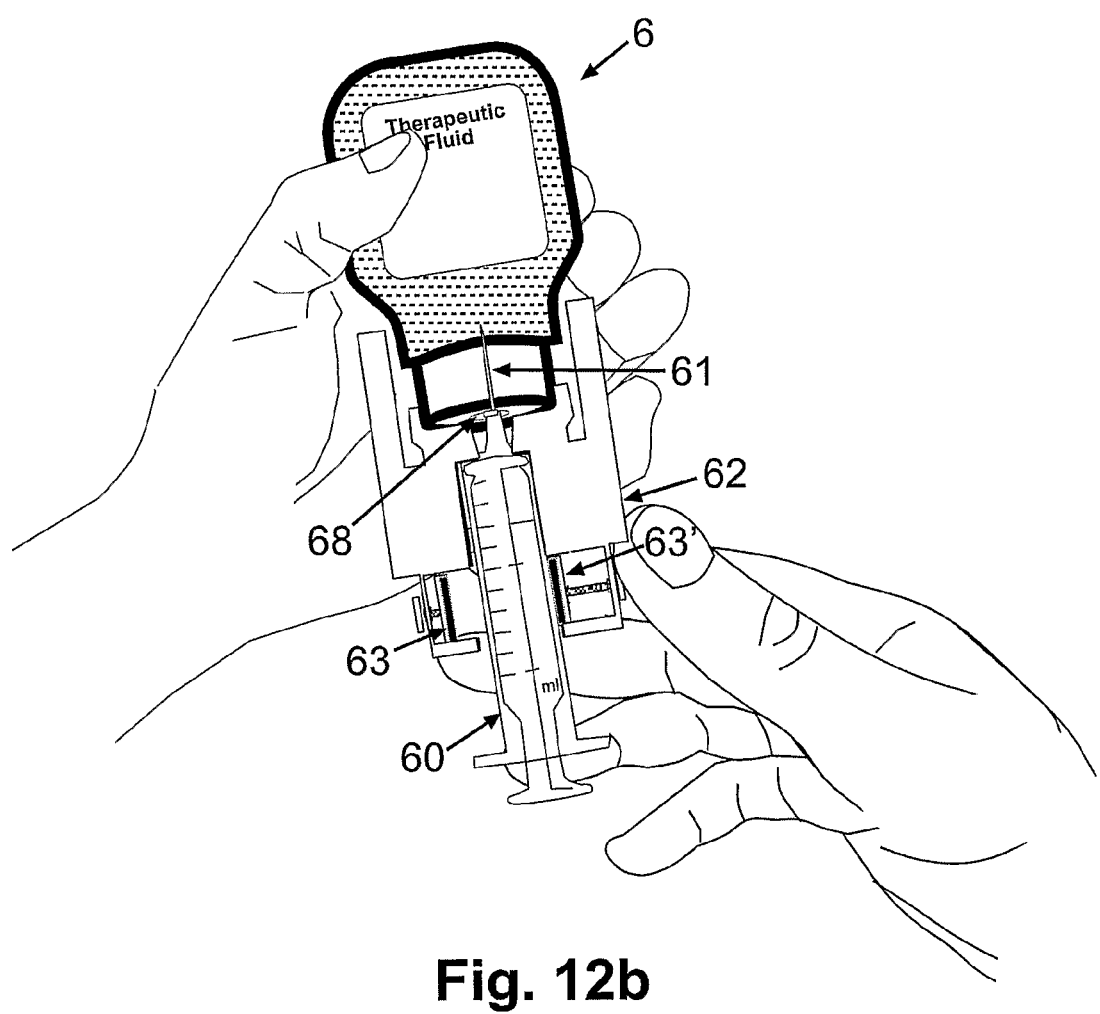
Figure 12C:
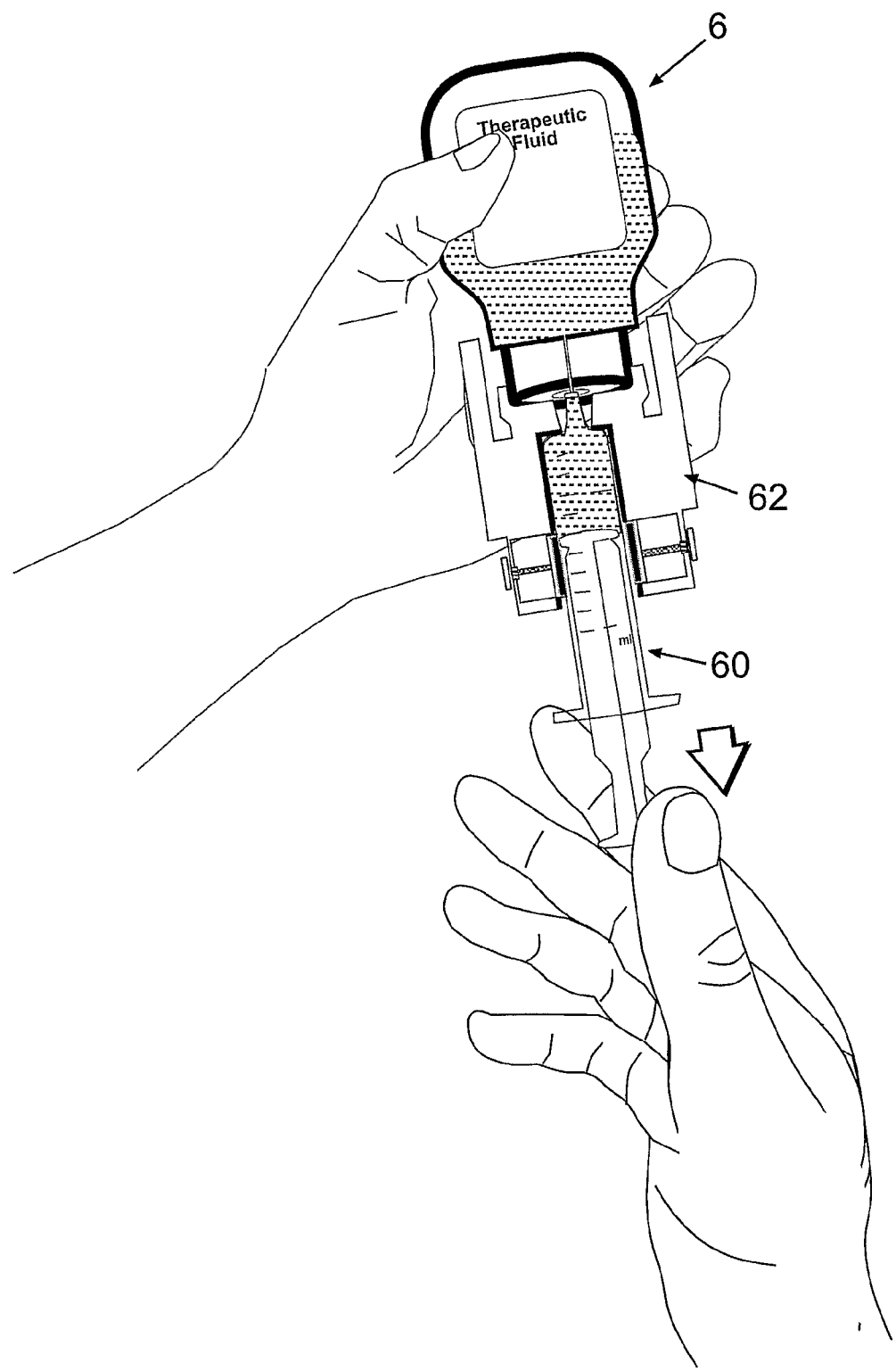
Figure 12D:
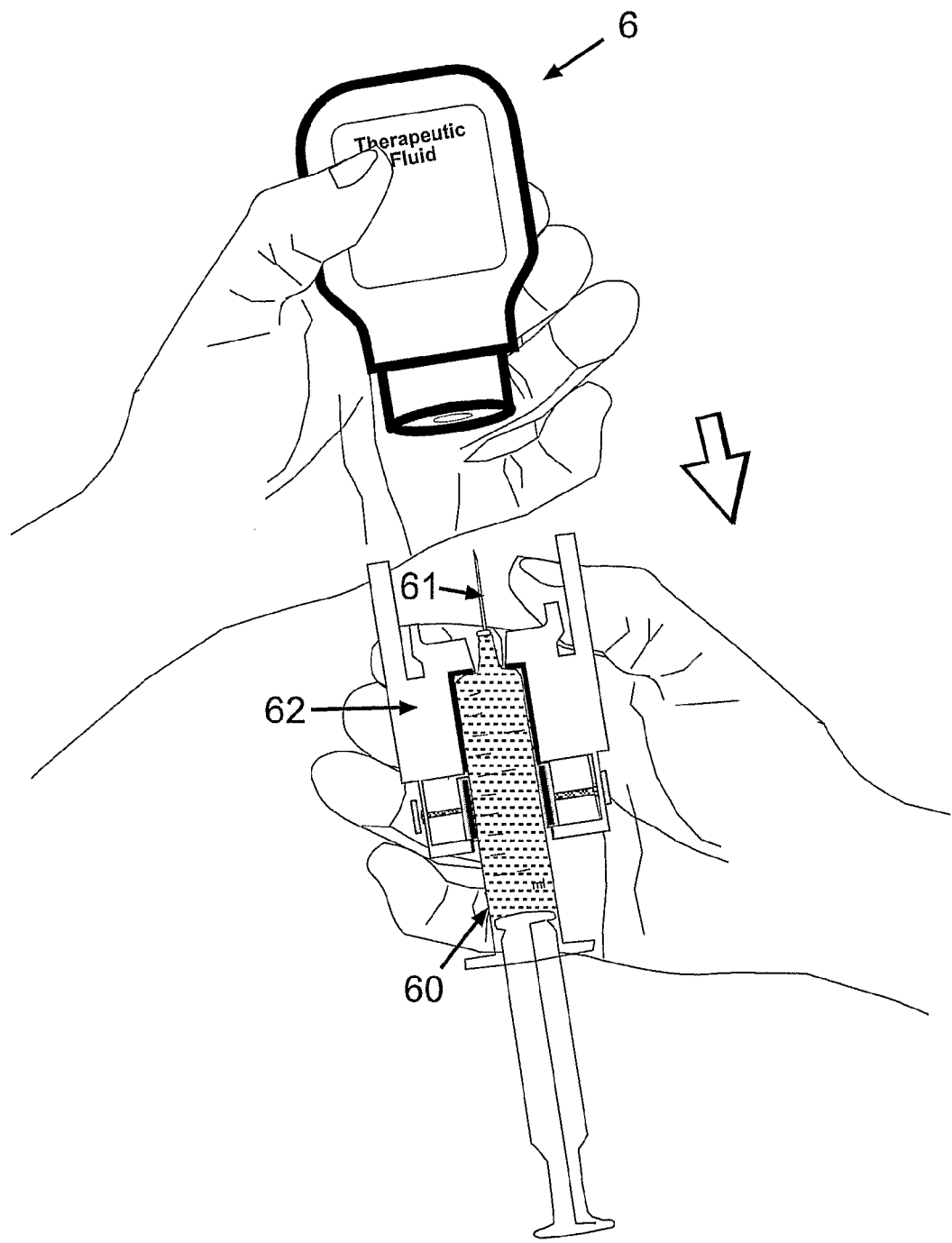
Figure 12E:
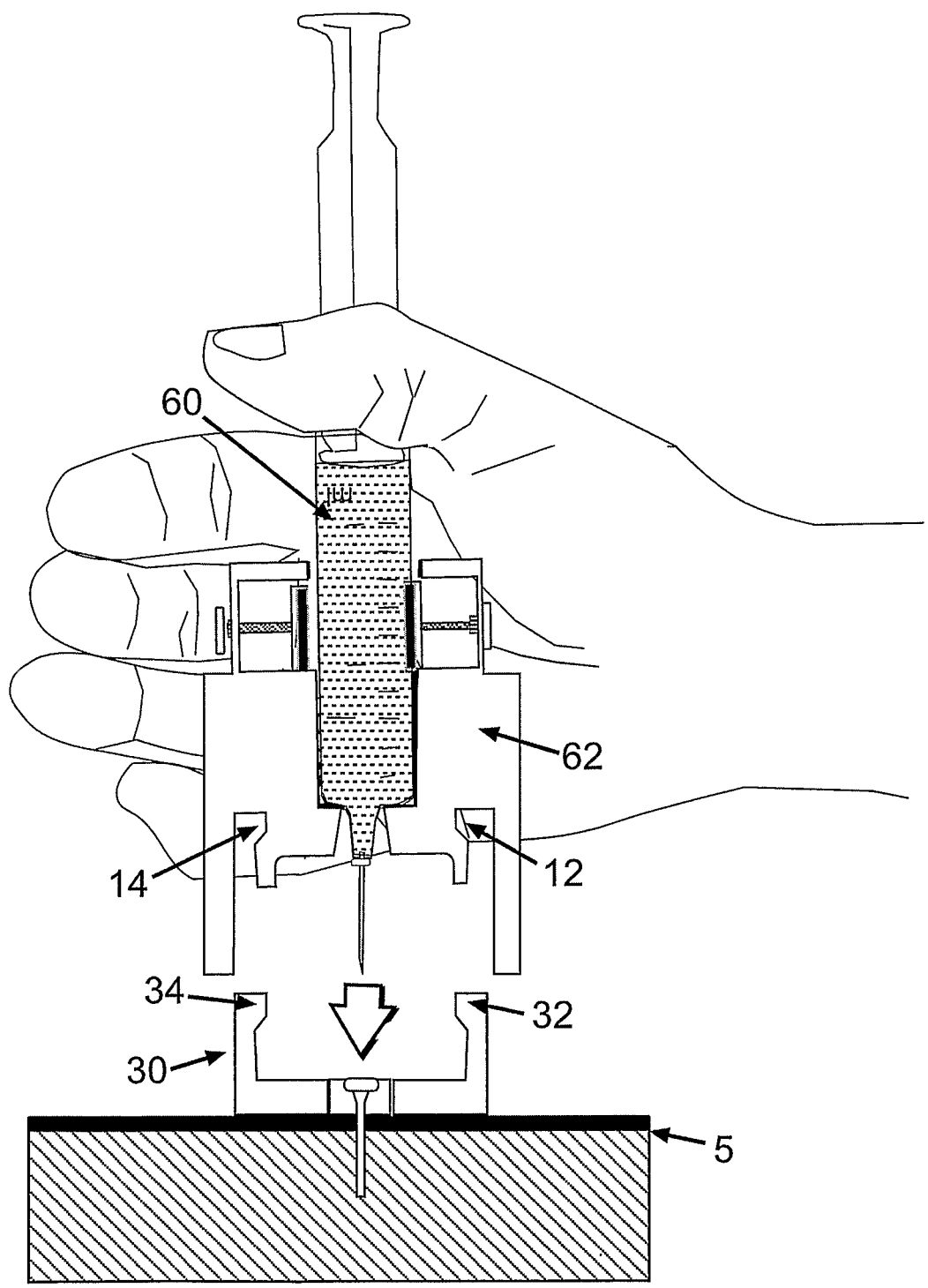
Figure 12F:
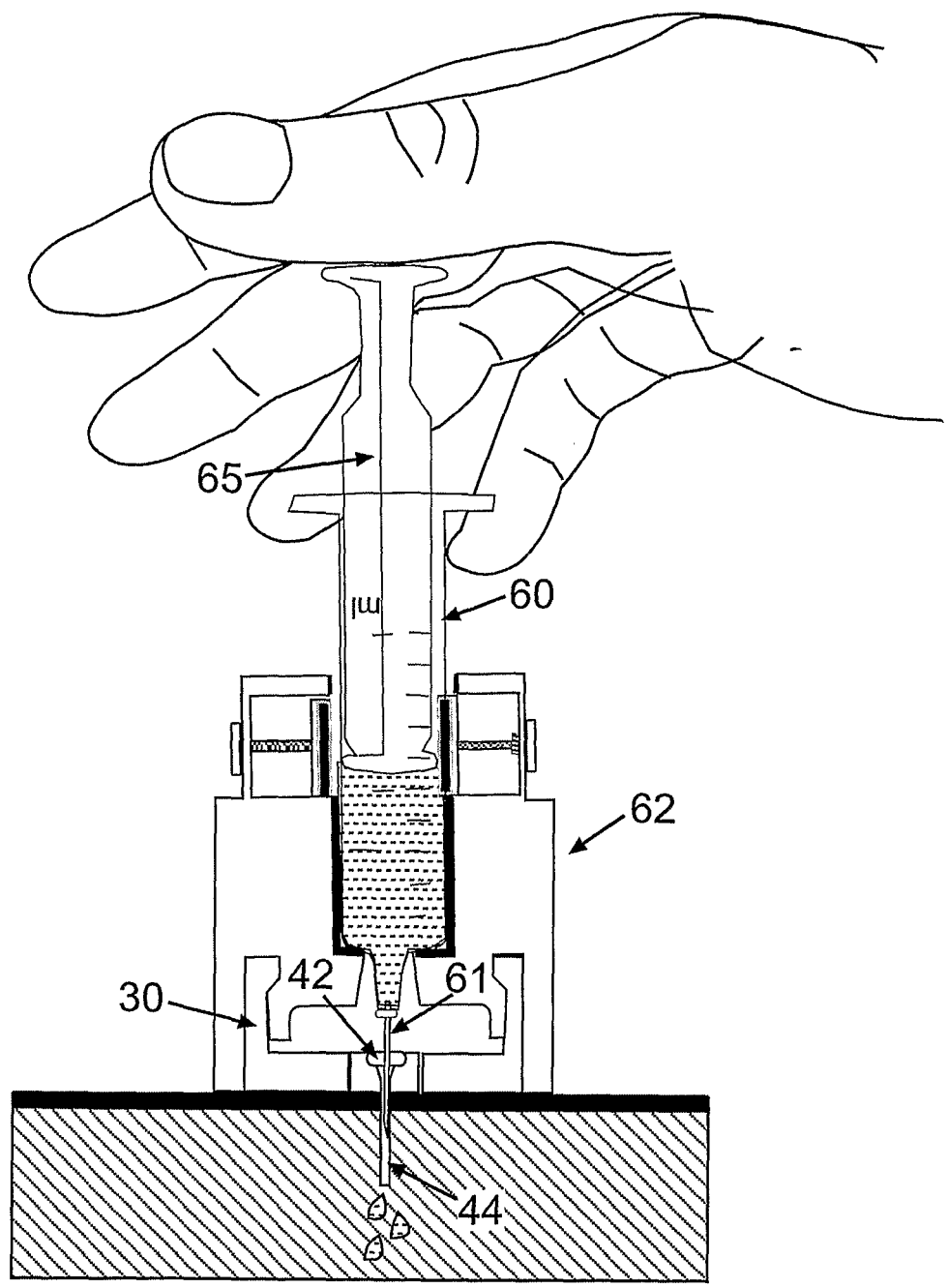
Figure 12G:
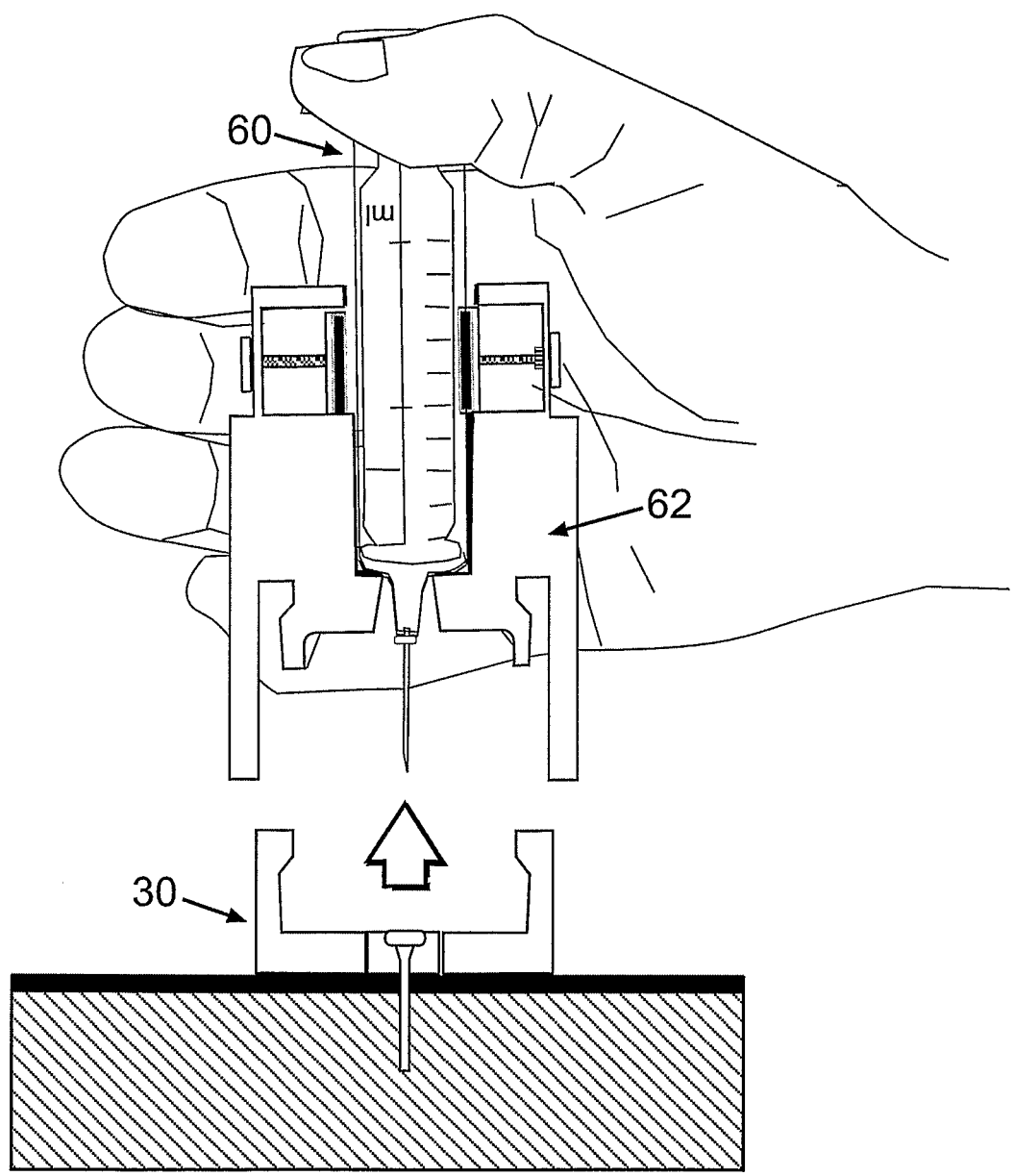

FIG. 12a shows an adapter 62, a vial 6 and a syringe 60 prior to connection. FIG. 12b shows the adapter 62 connected to the vial 6 and to the syringe 60. The syringe's needle 61 pierces the vial's septum 68. The syringe 60 may be secured in its place by, for example, two moveable fixators 63 and 63'. FIG. 12c shows fluid withdrawal from the vial 6 and the filling of the syringe 60. FIG. 12d shows the disconnection of the vial 6 from the adapter 62 and the syringe 60. The syringe's needle 61 may be enclosed (and thus concealed) within the adapter 62, thus providing the user with protection from unintentional pricking. FIG. 12e shows the syringe 60 and the adapter 62 prior to connection to the mounting housing 30. Under these circumstances, the connection may be performed by engagement of latches 32 and 34 extending from the housing 30 with corresponding recesses 12 and 14 on the adapter 62. FIG. 12f shows the adapter 62 and the syringe 60 connected to the housing 30. The syringe's needle 61 pierces the self-sealable septum 42 and the user then pushes the plunger 65, causing fluid to be delivered into the patient's body via the cannula 44. FIG. 12g shows the disconnection of the adapter 62 and syringe 60 from the housing 30 after completion of fluid delivery.

Figure 13A:
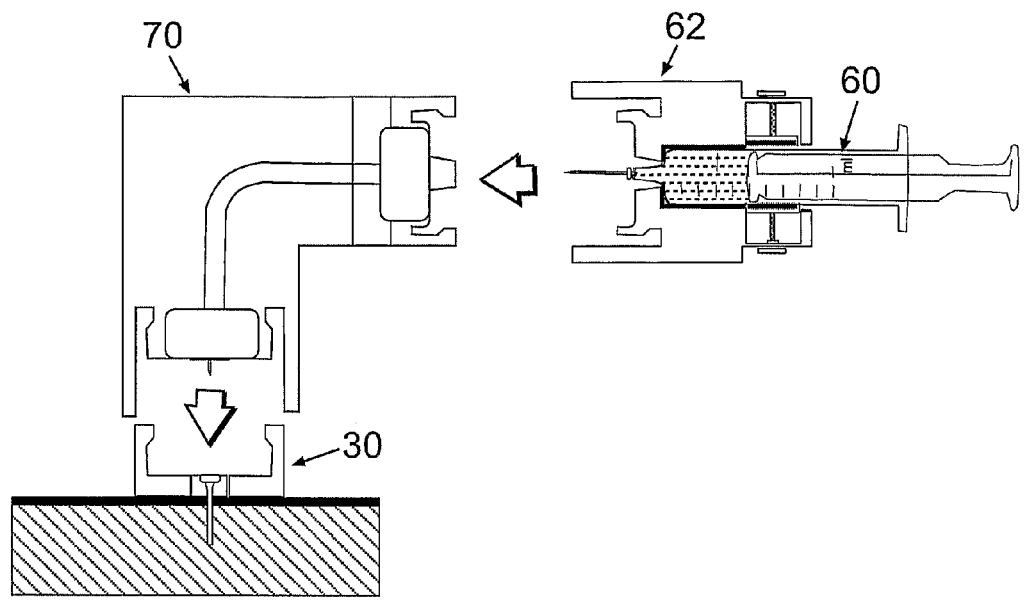
FIGS. 13a-b are schematic diagrams of an exemplary angular adapter.

Referring to FIG. 13a, a schematic diagram of an embodiment of an angular adapter 70 which can be connected to the adapter 62 and a syringe 60 on one end and to the mounting housing 30 on the other end is shown. The angular adapter 70 is intended to facilitate fluid injection in difficult angles, e.g., when the mounting housing 30 is secured to the patient's back or buttocks. The adapter 70 may be fabricated of a rigid material, e.g., plastic, or it may be fabricated, at least in part, using a flexible material, e.g., rubber, for more convenient usage.

Figure 13B:
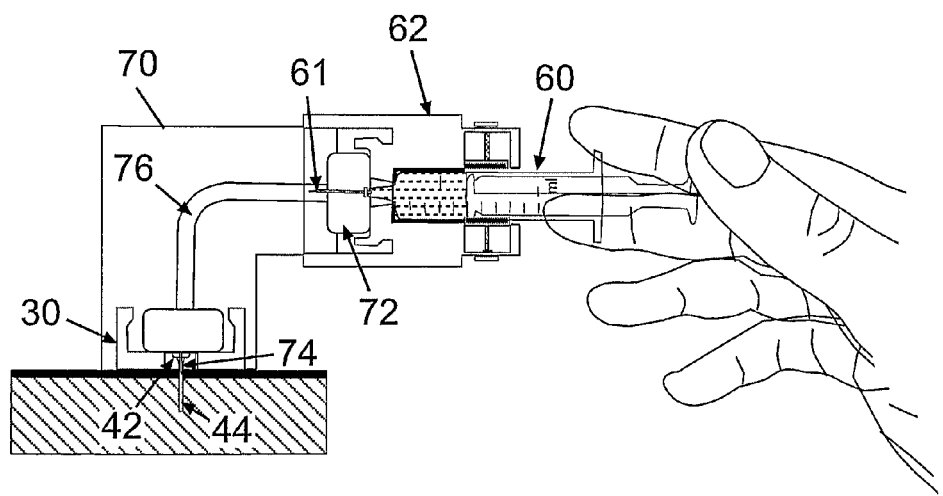

FIG. 13b shows the angular adapter 70 connected to the adapter 62 and the syringe 60 on one end and to the mounting housing 30 on the other end. The syringe's needle 61 pierces a septum 72 of the angular adapter 70 and a connecting lumen 74 pierces the septum 42 in the housing 30, thus enabling fluid to be delivered from the syringe 60 to the body via a connecting tube 76 and a cannula 44.

Referring to FIGS. 14a-d, schematic diagrams of an exemplary attachment and fluid injection procedure using a concave mounting housing 30 and a dedicated syringe 64 with a convex bottom portion are shown.

Figure 14A:
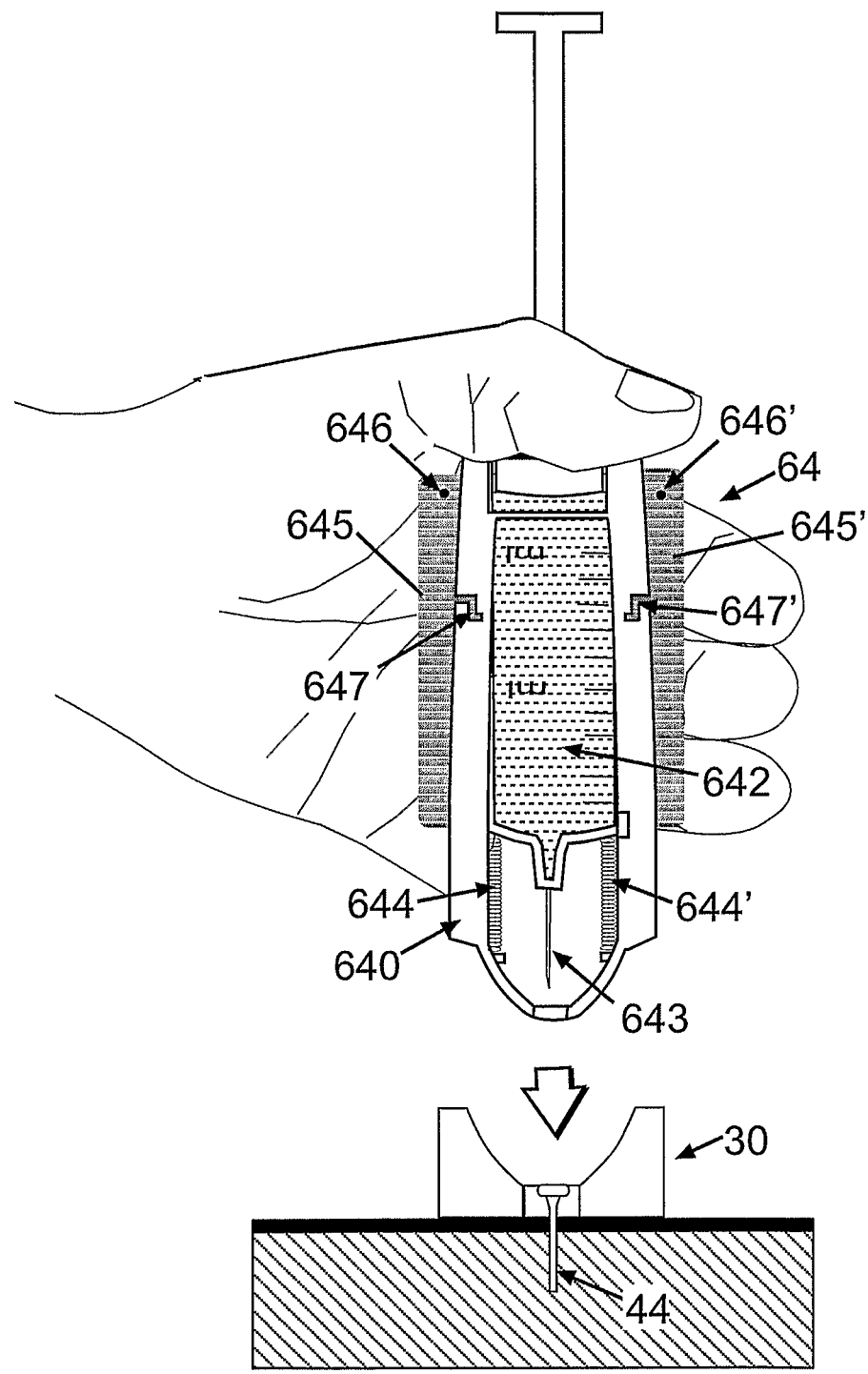
FIGS. 14a-d are views and diagrams illustrating exemplary operations of fluid injection using a concave mounting housing and a dedicated syringe with a convex bottom.

FIG. 14a shows the dedicated syringe 64 and the mounting housing 30 before connection. The dedicated syringe 64 may be provided with a housing 640 having a convex bottom portion that fits within a complementary concaved depression defined on the mounting housing 30 to facilitate alignment between the syringe needle 643 and the cannula 44. The housing of the syringe 640 may be also configured to enclose the syringe needle 643 so that the user is protected from unintentional pricking. One or more springs 644 and 644', which are connected to the syringe container 642 on one end and to the housing 640 on the other end, ensure that the needle 643 remains enclosed before and after use. After connecting the dedicated syringe 64 to the mounting housing 30, the user manually inserts the needle 643 to the cannula 44 by pressing two lateral spring handles 645 and 645', which are rigidly connected to the syringe container (642) via dedicated grooves (not seen) in the housing 640, and pushing them downwards. The lateral handles 645 and 645' are each provided with a dedicated rod (646 and 646') which may be captured by corresponding notches 647 and 647' in the housing 640 to secure the syringe container 642 and needle 643 are in their place during fluid injection.

Figure 14B:
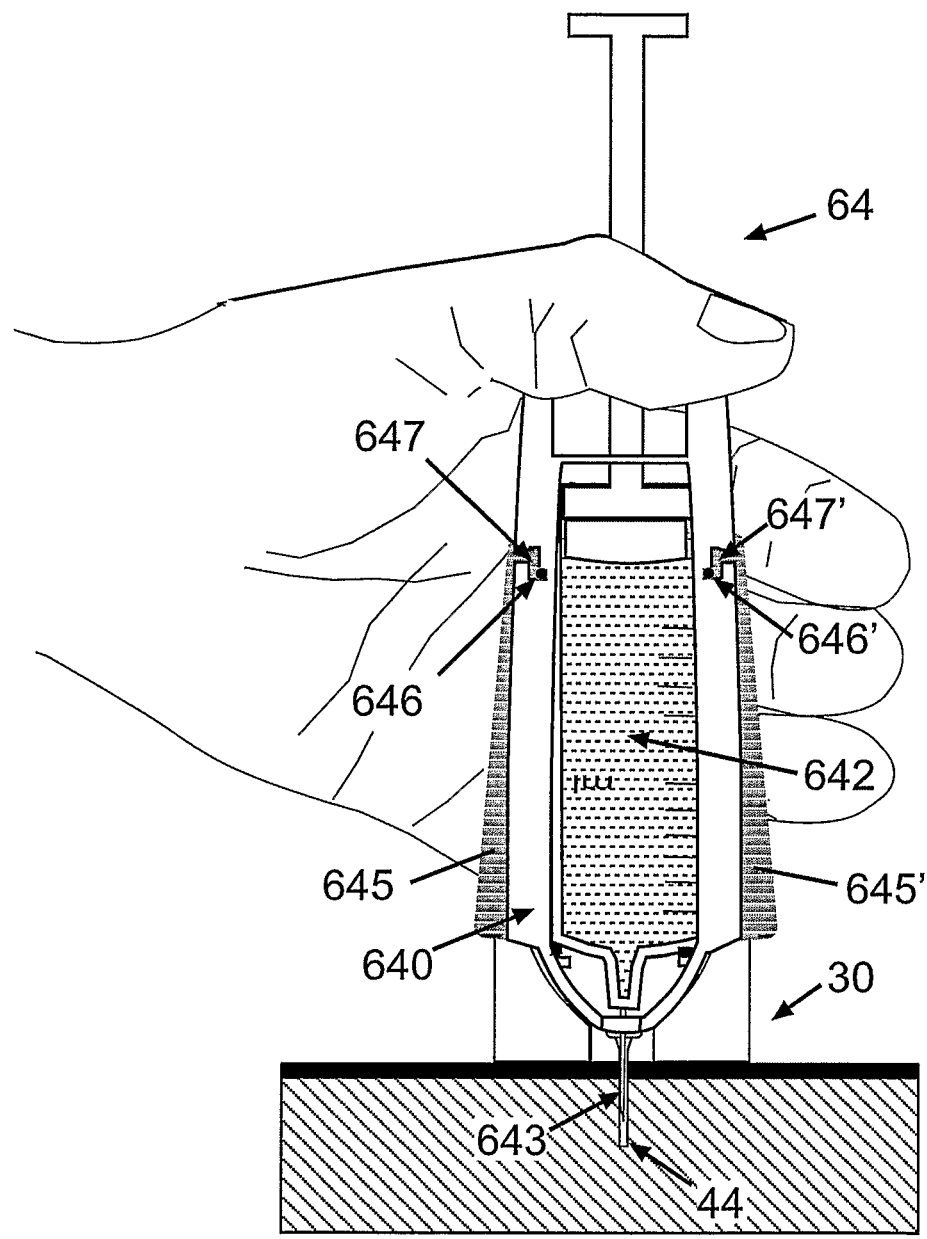

FIG. 14b shows the dedicated syringe 64 connected to the housing 30. The syringe needle 643 may be inserted in the cannula 44, and the syringe container 642 may be secured in its place by a capturing engagement of the handles' dedicated rods 646 and 646' with their respective notches (647 and 647').

Figure 14C:
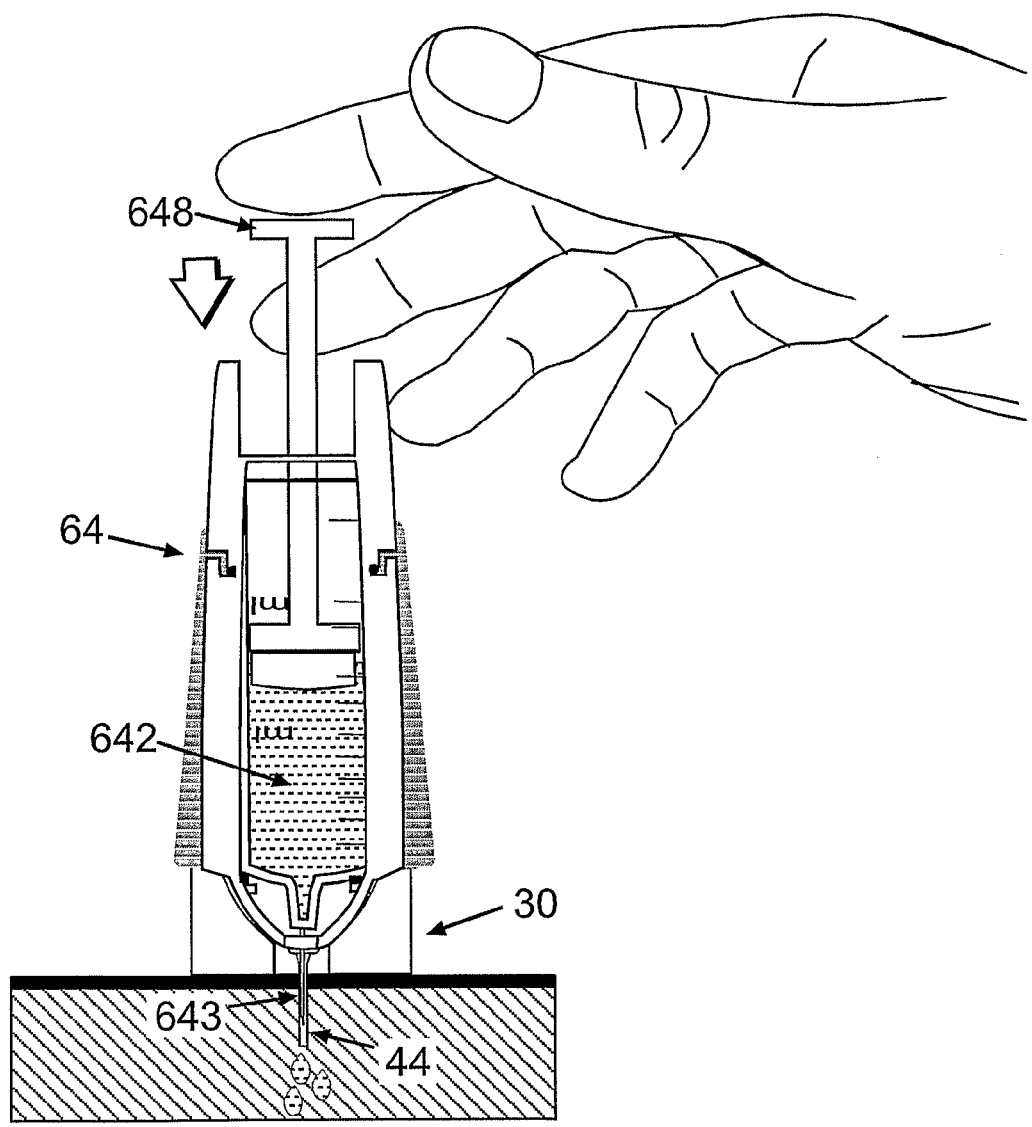

FIG. 14c shows the plunger 648 being pressed and fluid being injected into the subcutaneous compartment via the cannula 44.

Figure 14D:
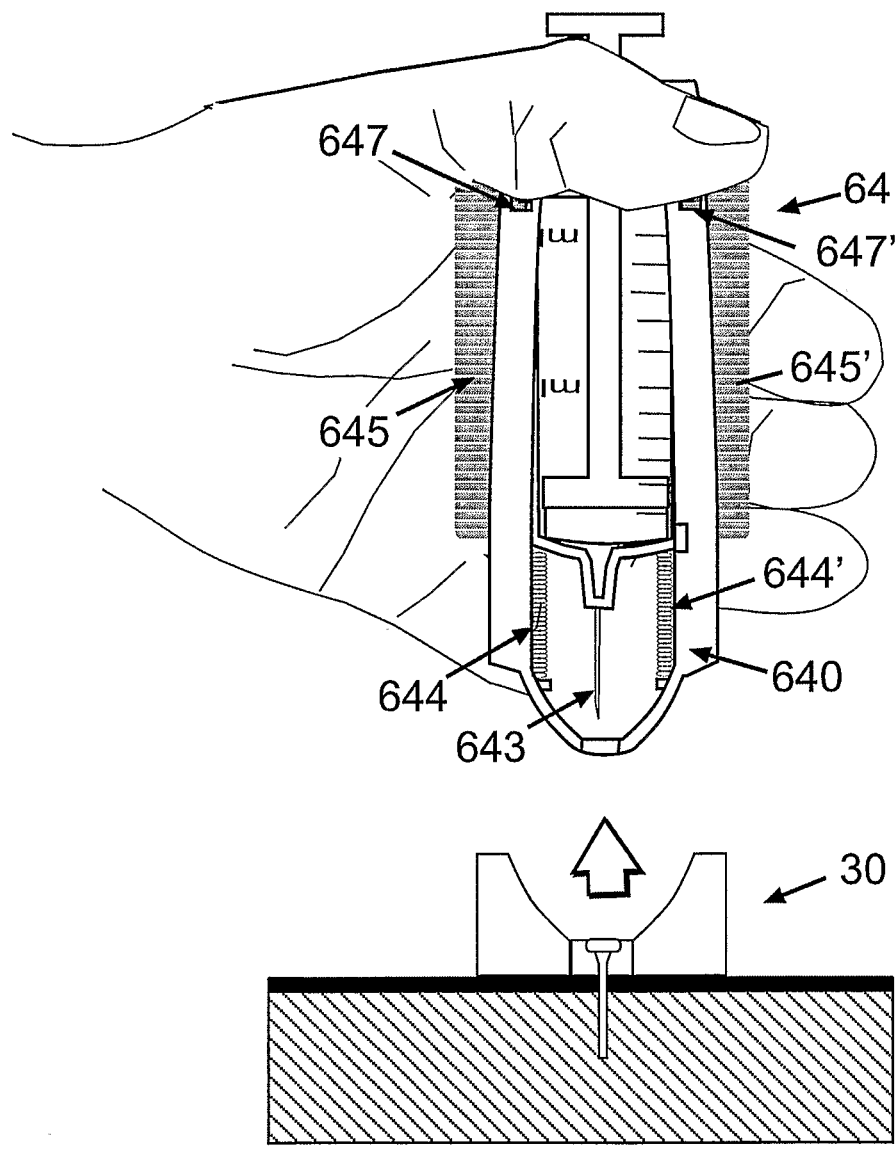

FIG. 14d shows the dedicated syringe 64 being disconnected from the mounting housing 30. After fluid injection is completed, the user presses the lateral handles 645 and 645' to release the dedicated rods from the notches 647 and 647'. The springs 644 and 644' can then return to their unloaded state, thus pushing upwards the syringe container 642 and retracting the needle 643 back into the syringe housing 640. The user then disconnects the dedicated syringe 64 from the mounting housing 30.

Under some circumstances, the user may prefer that the therapeutic device (e.g., delivery device) remain connected to the housing 30 even when the device is not operating (e.g., when fluid is not being delivered), for example, when there is no accessible location for safely storing the device between consecutive activations, or when the user wishes to connect to the mounting housing 30 an infusion pump for continuous drug delivery without being required to hold it in its place, which is both inconvenient and impractical. In such scenarios, a dedicated skin-securable (e.g., adherable) cradle 20 may be provided, which may be coupled to the mounting housing 30, as more particularly described below in FIGS. 15-16.

Figure 15A:
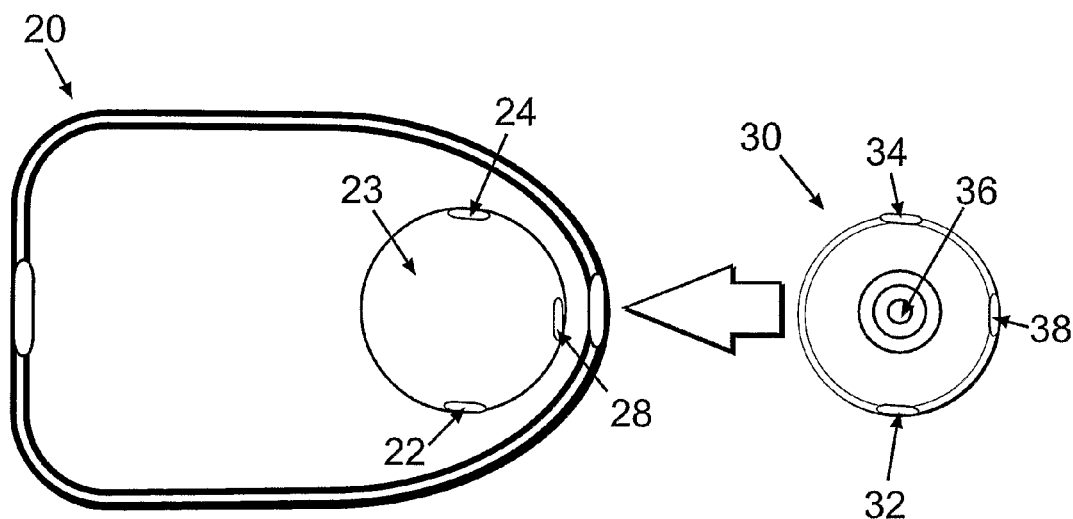
FIGS. 15a-b are diagrams of an exemplary mounting housing and a dedicated cradle before and after connection of the two.

FIG. 15a is a schematic diagram of an exemplary embodiment of a mounting housing 30 and a dedicated cradle 20 prior to connection. A cradle is a device to removeably connect a therapeutic device (e.g., a delivery device and/or a sensing device) to the user's skin to enable easy connection and disconnection of the therapeutic device at the user's discretion. A description of a cradle is described in co-owned U.S. Provisional Patent Application No. 60/876,679, filed Dec. 22, 2006, the content of which is hereby incorporated by reference in its entirety. The dedicated cradle 20 may be configured as a flat plate with an adhesive layer covering the cradle's contact surface facing the skin. The cradle may also be provided with a dedicated depression or recess 23 substantially matching the size and shape of the mounting housing 30. Connection between the two structures may thus be established by, for example, a snapping engagement of one or more latches, in this case latches 32, 34 and 38, in the mounting housing 30 with respective indentations 22, 24 and 28 in the cradle 20.

Figure 15B:
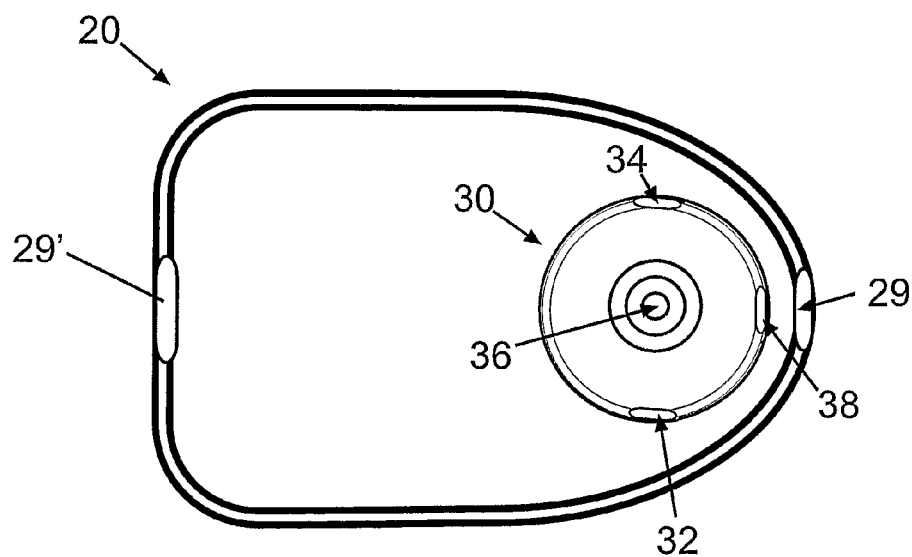

FIG. 15b shows the mounting housing 30 connected to the cradle 20. After connecting the two structures, a therapeutic device can be connected to the cradle 20 and the mounting housing 30 with connecting mechanisms 29 and 29' provided on the cradle's 20 upper side. The therapeutic device (e.g., delivery device) can be either a device for bolus doses delivery, a device for continuous (or periodic) drug delivery (e.g., basal delivery) or a device for both basal and bolus deliveries.

The mounting housing 30 and the cradle 20 units may be connected to each other prior to securing of the housing to the patient's skin, or after securing of the mounting housing 30 to the patient's skin and insertion of a cannula into the body.

Figure 16A:
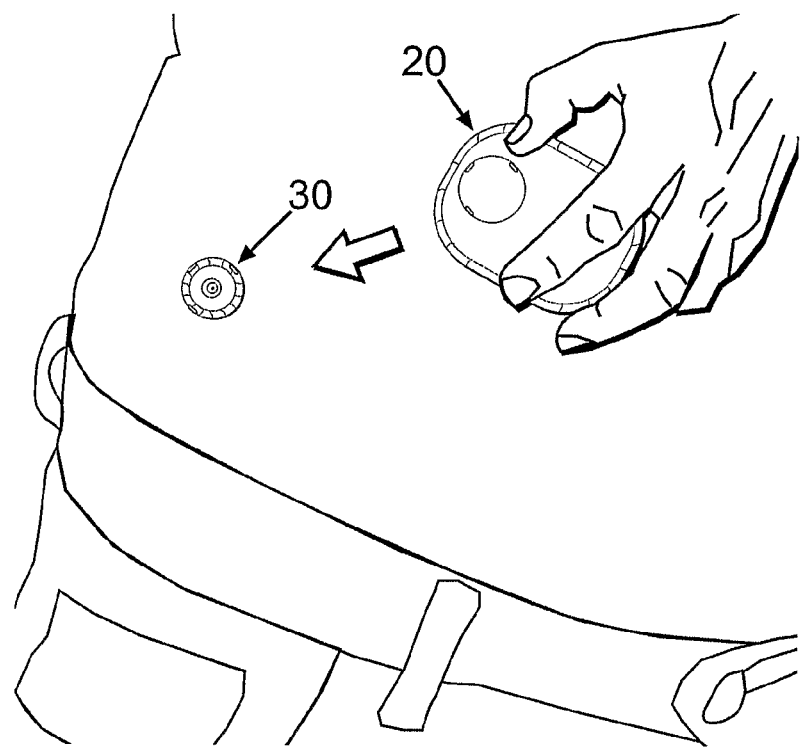
FIGS. 16a-d are views illustrating connection of a dedicated cradle to a mounting housing adhered to the skin, and connection of a fluid delivery device to the connected mounting housing and cradle.
Figure 16B:
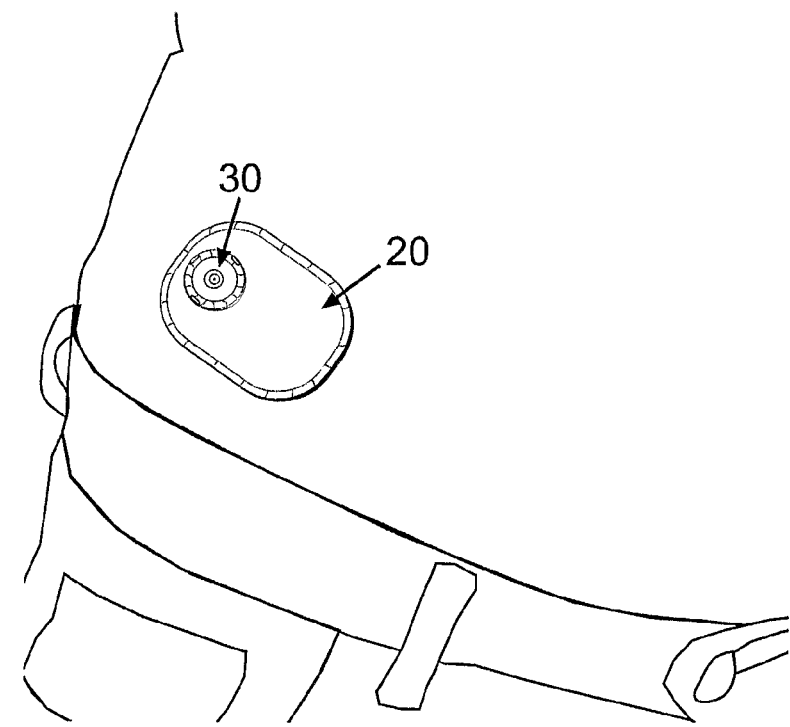
Figure 16C:
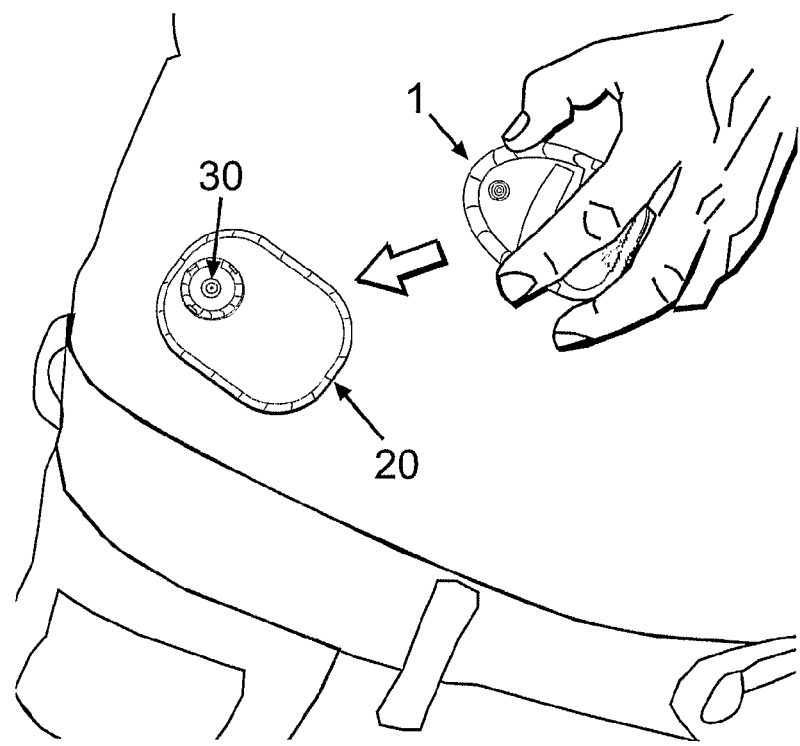
Figure 16D:
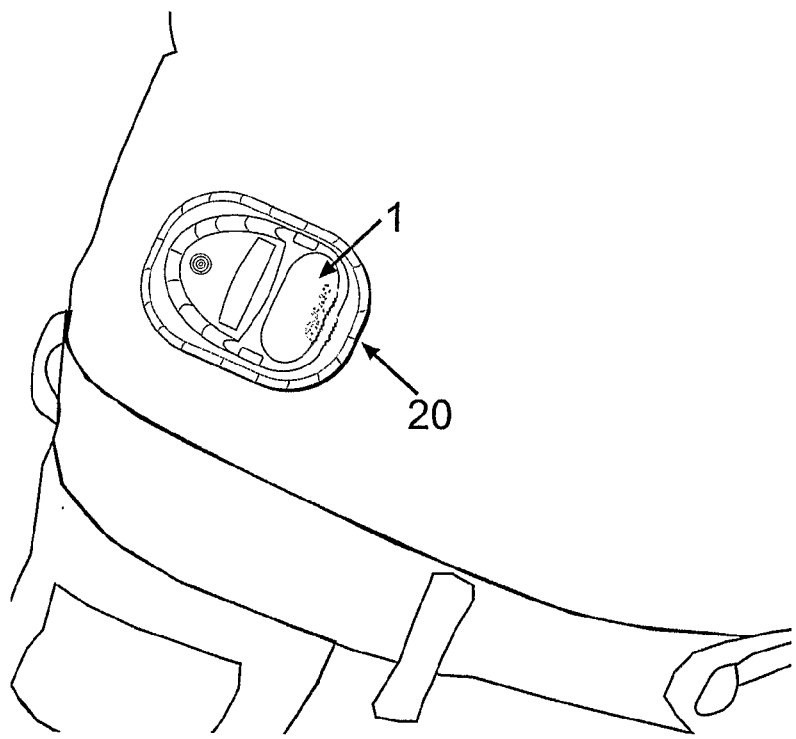

FIG. 16a shows a dedicated cradle 20 connected to a mounting housing 30 which has already been secured (e.g., adhered) to the skin. FIG. 16b shows a cradle 20 connected to a housing 30, both of which are adhered to the skin. The cradle 20 can be connected to and disconnected from the mounting housing 30 while the latter remains secured to the patient's skin and the cannula remains in the subcutaneous compartment. FIG. 16c shows a fluid delivery device 1 being connected to the mounting housing 30 and cradle 20 (after cannula insertion). FIG. 16d shows a fluid delivery device 1 connected to the mounting housing 30 and cradle 20 and ready for operation.

Figure 17A:
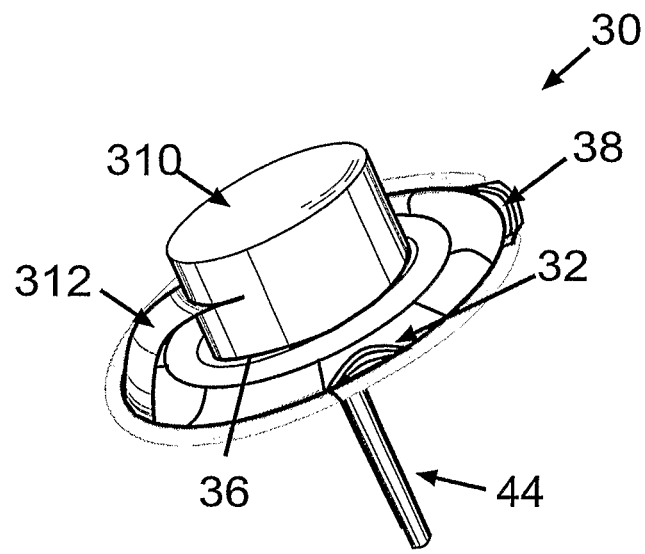
FIGS. 17a-b are perspective views of an exemplary housing with a protective cap.
Figure 17B:
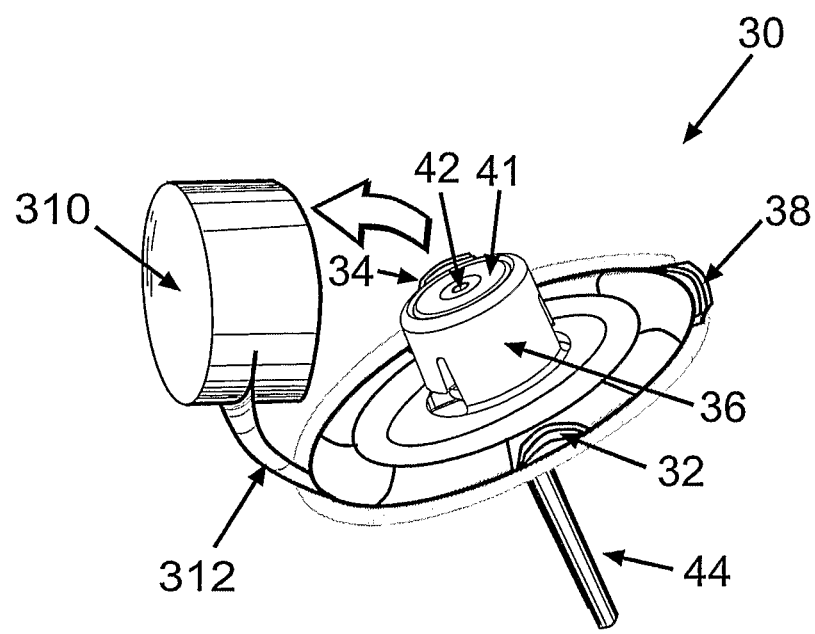

Referring to FIG. 17a, a perspective view of an exemplary mounting housing 30 that includes a protective cap 310 is shown. The cap 310 may be connected to the housing 30 with a connector 312, or it may be a separate item. The protective cap 310 protects the passageway 36 (which may be defined by a well) and the cannula hub 41 with its septum 42 from damage and accumulation of dirt, which may prevent proper connection of a delivery device to the mounting housing 30. FIG. 17b shows the protective cap 310 being removed to thus enable connection to a therapeutic device (e.g., a fluid delivery device).

The assembly/device that includes a mounting housing securable to the skin of a patient may be used in conjunction with delivery devices which are not directly connected to the mounting housing 30. Such devices may be, for example, a pager-like infusion pump that may be carried in the user's pocket or on the belt, or a skin adherable infusion device. A connector, such as an infusion set connector 600 may be used to establish a connection between the delivery device and the mounting housing 30.

Figure 18A:
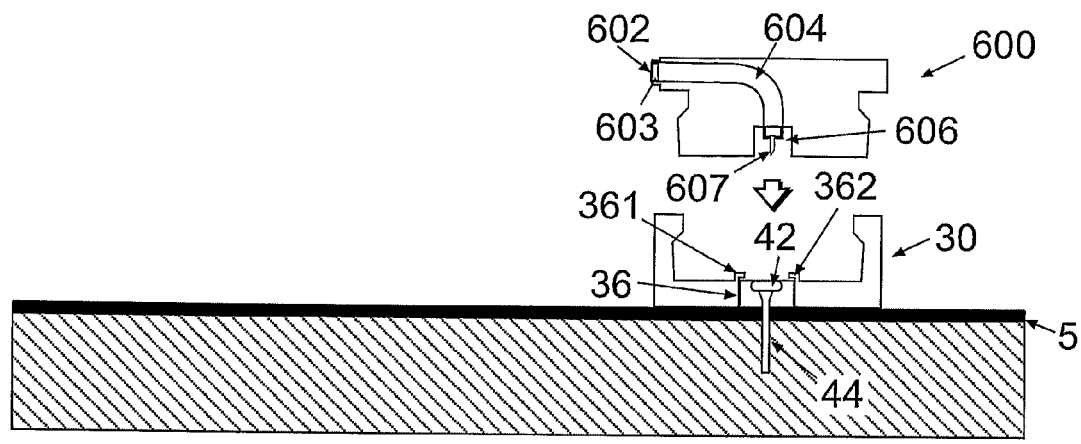
FIGS. 18a-b are schematic diagrams of an exemplary infusion set connector connecting a skin adherable infusion pump to a mounting housing.

FIG. 18a shows a mounting housing 30 and an infusion set connector 600. The connector 600 includes an inlet port 602 and an outlet port 606. The inlet port 602 may be provided with a septum 603, which can be repeatedly pierced by a delivery device's needle (not shown in FIG. 18a). The outlet port 606 may be provided with a connecting lumen 607, which can repeatedly pierce the cannula hub's septum 42. The inlet 602 and outlet 606 ports are bridged by a tube 604 which enables passage of fluid from the delivery device to the cannula 44 via the tube 604 to the patient's body.

Figure 18B:
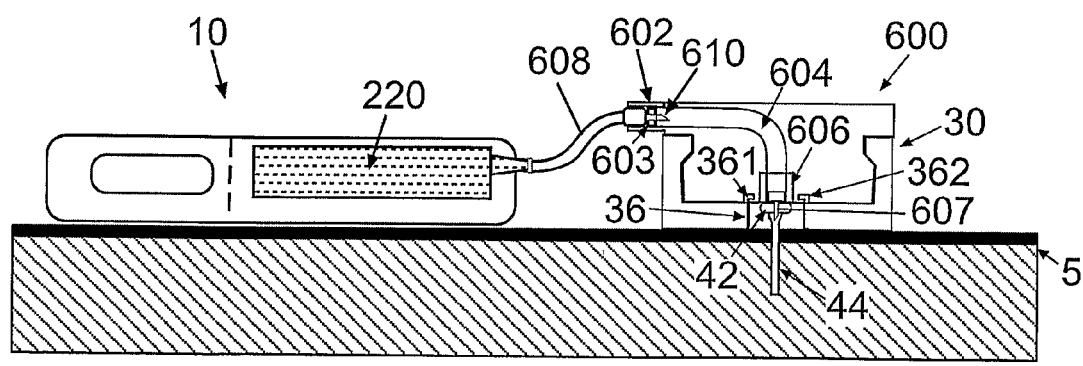

FIG. 18b shows an infusion set connector 600 connecting a skin adherable infusion pump 10 to a mounting housing 30. The infusion pump 10 may be connected to the inlet port 602 via an external tube 608 and a connecting needle 610 which pierces the inlet port's septum 603. Fluid passes from the reservoir 220 through the infusion set connector 600 and to the patient's body FIG. 19a shows a sensing device 2 connected to a mounting housing 30. One or more analyte (e.g., glucose) detectors 90 are provided on the cannula 44 and are connected to a sensing apparatus 202 in the device 2 via two sets of connectors 92 and 94. One set 92 may be located on the cannula hub 41 and on the housing's 30 well, and the other set 94 may be located on the housing's 30 base and on the sensing device 2. The device 2 may also comprise a processor/controller 201, an energy source 204, a display 205 and user-actuated operating buttons 206. In some embodiments, the device includes a fluid (e.g., insulin) dispensing module 203, which may operate independently from the sensing module 202, and/or may operate in a semi closed-loop mode, or in a full closed-loop mode. After connecting the sensing device 2 to the mounting housing 30, electrical signals from the analyte (e.g., glucose) detectors 90 are transmitted continuously or periodically to the sensing device 2. After processing the signals by the processor/controller 201 the analyte concentration levels may be determined and presented on the display 205.

Figure 19B:
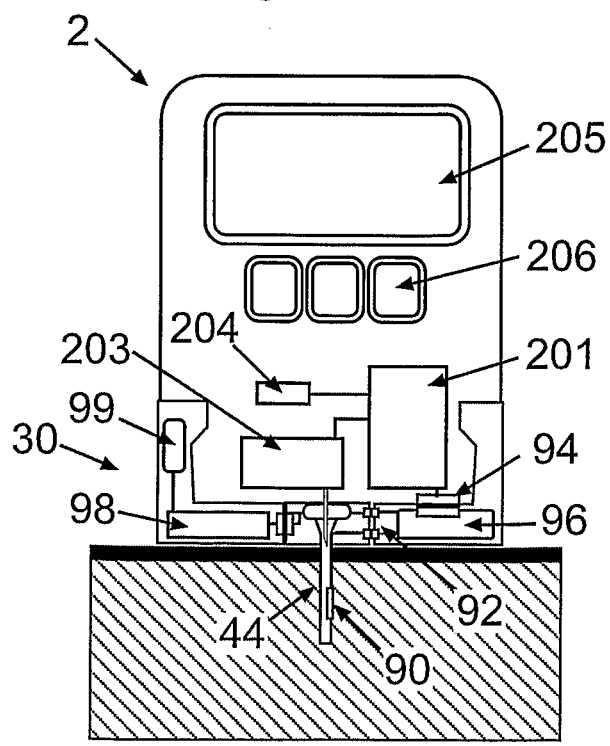

FIG. 19b shows an exemplary embodiment in which the mounting housing 30 includes a sensing apparatus 96, a processor/controller 98 and an energy source 99. In some embodiments, analyte (e.g., glucose) levels are sensed and determined continuously or periodically, and upon connection of a sensing device 2 the sensing data may be transmitted to the device 2 via two sets of connectors 92 and 94. The sensing device 2 includes a processor/controller 201 and an energy source 204, and, in some embodiments, may include operating buttons 206 and a display 205. The sensing device 2 can also include a dispensing apparatus 203.

Figure 19C:
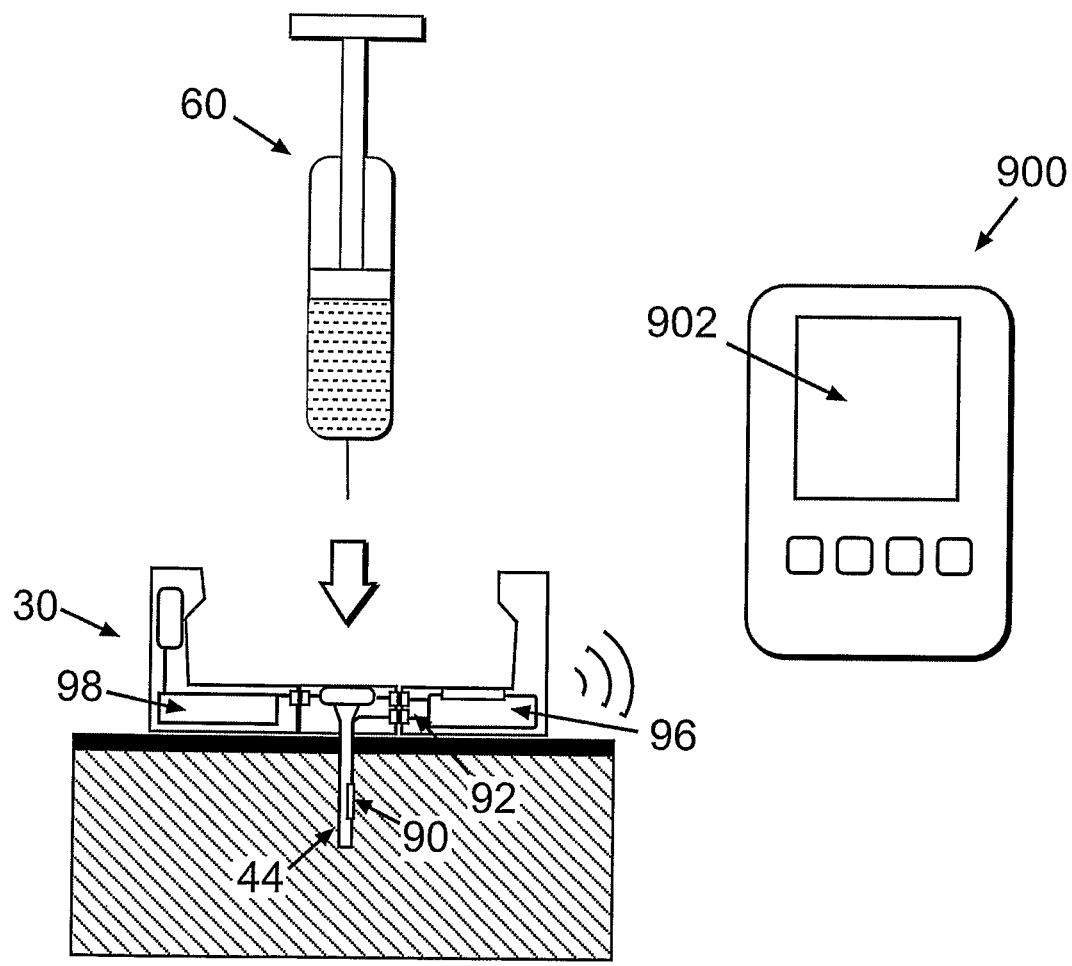

Referring to FIG. 19c, a schematic diagram of a processor/controller 96 included in the mounting housing 30 and which further includes a transceiver is shown. Analyte (e.g., glucose) levels are sensed continuously or periodically, and the sensing data may be transmitted wirelessly to a remote control unit 900 and it may be presented on the remote control unit's screen 902. A fluid delivery device such as a syringe 60, or an infusion pump (not shown), may be connected to the mounting housing 30 as needed.

Any and all patents, applications, articles and/or publications referenced in this specification are hereby incorporated by reference herein in their entireties.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, presently unclaimed inventions are also contemplated.

What is claimed is:

1. A therapeutic subcutaneous access apparatus for intermittently receiving a portable therapeutic device and adapted for at least one of delivering a therapeutic fluid into the body of a patient and sensing a bodily analyte, the therapeutic subcutaneous access apparatus comprising:
- a housing configured to be securable to the skin of a patient;
- a skin-securable cradle having a support surface for securing to the skin of the patient and a recess defined in the support surface for receiving and surrounding the housing to enable connection of the portable therapeutic device to the therapeutic subcutaneous access apparatus; and
- a cannula insertable through a passageway provided within the housing so that at least a portion of the cannula is subcutaneously placed in the body of the patient, wherein:
- the housing comprises a well defining the passageway, the well being configured to tilt relative to a surface of the housing that contacts the skin of the patient when the housing is secured to the skin of the patient, for enabling insertion of the cannula at an angle,
- the well includes a tilting mechanism to control the angle of tilt of the well, the tilting mechanism comprising one or more rods, at least one of the one or more rods having a first end attached to the well and a second end attached to a gear rotatable within a corresponding groove defined in a base of the housing, wherein the groove includes a first section in which the gear can be rotated, a second section into which the gear is placed to lock the gear and well into place, and the second section is narrower than the first section;
- the cannula is configured for insertion through the passageway subsequent to securing of the housing to the skin of the patient, and
- the cannula is configured for rigid connection to the housing in a substantially locking configuration upon insertion of the cannula through the passageway.

2. The therapeutic subcutaneous access apparatus according to claim 1, wherein the cannula is inserted through the passageway at a predetermined angle with respect to the surface of the skin of the patient.

3. The therapeutic subcutaneous access apparatus according to claim 1, wherein the cannula is configured for delivering therapeutic fluid.

4. The therapeutic subcutaneous access apparatus according to claim 3, wherein the therapeutic fluid comprises insulin.

5. The therapeutic subcutaneous access apparatus according to claim 1, wherein the cannula is configured for sensing a bodily analyte.

6. The therapeutic subcutaneous access apparatus according to claim 5, wherein the bodily analyte comprises one or more of glucose and ketones.

7. The therapeutic subcutaneous access apparatus according to claim 1, wherein the therapeutic subcutaneous access apparatus is further configured for use with an insertion device for inserting the cannula through the passageway so as to place at least a portion of the cannula subcutaneously in the body of the patient.

8. The therapeutic subcutaneous access apparatus according to claim 1, wherein the cannula further comprises a cannula hub attached to the cannula.

9. The therapeutic subcutaneous access apparatus according to claim 1, wherein the cannula further comprises a self-sealing septum provided on a proximal end thereof.

10. The therapeutic subcutaneous access apparatus according to claim 1, wherein the cannula further comprises a penetrating member having a grip portion.

11. The therapeutic subcutaneous access apparatus according to claim 8, wherein the housing further comprises:
- one or more anchors to rigidly connect the cannula hub to the housing, the one or more anchors positioned proximate to the passageway.

12. The therapeutic subcutaneous access apparatus according to claim 1, wherein the housing further comprises an adhesive to secure the housing to the body of the patient.

13. The therapeutic subcutaneous access apparatus according to claim 1, wherein the portable therapeutic device comprises a fluid delivery device selected from the group consisting of: a standard syringe, a syringe fitted within an adapter coupleable to the therapeutic apparatus, a jet pen, a single-part infusion device and a two-part infusion device.

14. The therapeutic subcutaneous access apparatus according to claim 1, wherein the portable therapeutic device comprises a sensing device.

15. The therapeutic subcutaneous access apparatus according to claim 14, wherein the cannula is further configured for coupling to a sensor configured to sense analytes in the body of the patient, the sensor further configured to communicate with the sensing device.

16. The therapeutic subcutaneous access apparatus according to claim 15 wherein the sensor comprises one or more of: an optical sensor, an electrochemical sensor, an acoustic sensor and a Continuous Glucose Monitor (CGM).

17. The therapeutic subcutaneous access apparatus according to claim 15, wherein the sensor comprises at least one electrode configured to generate a signal representative of a concentration of the bodily analyte.

18. The therapeutic subcutaneous access apparatus according to claim 17, wherein at least one of the housing and the cannula comprises a communication module to transmit the signal.

19. The therapeutic subcutaneous access apparatus according to claim 17, wherein the communications module communicates via at least one of a wired and a wireless connection.

20. The therapeutic subcutaneous access apparatus according to claim 1, wherein the housing is configured for facilitating alignment between the housing and the portable therapeutic device.

21. The therapeutic subcutaneous access apparatus according to claim 20, wherein the housing includes at least one locking latch for mating with at least one recess defined on the portable therapeutic device.

22. The therapeutic subcutaneous access apparatus according to claim 20, wherein the housing defines a concave depression to receive a convex-shaped section of a body of the portable therapeutic device.

23. The therapeutic subcutaneous access apparatus according to claim 20, wherein the housing includes magnetic material to enable magnetic connection with another magnetic material provided in or on at least one corresponding connecting area in the portable therapeutic device.

24. The therapeutic subcutaneous access apparatus according to claim 1, further including an adapter for connecting the portable therapeutic device to the housing.

25. The therapeutic subcutaneous access apparatus according to claim 24, wherein the adapter comprises an angular adapter to connect the portable therapeutic device to the therapeutic subcutaneous access apparatus at an angle.

26. The therapeutic subcutaneous access apparatus according to claim 13, further including a connector to establish fluid communication between the fluid delivery device and the therapeutic subcutaneous access apparatus.

27. The therapeutic subcutaneous access apparatus according to claim 1, wherein the housing is configured for fitting with a protective cover connectable to the housing to protect at least the passageway.

28. A therapeutic system for at least one of delivering a therapeutic fluid into the body of a patient and sensing a bodily analyte, the therapeutic system comprising:
a portable therapeutic device for at least one of delivering a therapeutic fluid into the body of a patient and sensing a bodily analyte;
a therapeutic subcutaneous access apparatus configured for intermittently receiving the portable therapeutic device, the therapeutic subcutaneous access apparatus comprising:
a housing configured to be securable to the skin of a patient;
a skin-securable cradle having a support surface for securing to the skin of the patient and a recess defined in the support surface for receiving and surrounding the housing to enable connection of the portable therapeutic device to the therapeutic subcutaneous access apparatus; and
a cannula insertable through a passageway provided within the housing so that at least a portion of the cannula is subcutaneously placed in the body of the patient,
wherein:
the housing comprises a well defining the passageway, the well is configured to tilt relative to a surface of the housing that contacts the skin of the patient when the housing is secured to the skin of the patient, for enabling insertion of the cannula at an angle,
the well includes a tilting mechanism to control the angle of tilt of the well, the tilting mechanism comprising one or more rods, at least one of the one or more rods having a first end attached to the well and a second end attached to a gear rotatable within a corresponding groove defined in a base of the housing, wherein the groove includes a first section in which the gear can be rotated, a second section into which the gear is placed to lock the gear and well into place, and the second section is narrower than the first section;
the cannula is configured for insertion through the passageway subsequent to securing of the housing to the skin of the patient, and
the cannula is configured for rigid connection to the housing in a substantially locking configuration upon insertion of the cannula through the passageway.

29. The therapeutic system according to claim 28, wherein a connecting area in the portable therapeutic device substantially corresponds to a connecting area in the therapeutic subcutaneous access apparatus to facilitate alignment between the portable therapeutic device and the therapeutic subcutaneous access apparatus.

30. The therapeutic system according to claim 29, wherein the connecting area in the portable therapeutic device includes at least one recess and the connecting area in the therapeutic subcutaneous access apparatus includes at least one locking latch for mating with at least one recess.

31. The therapeutic system according to claim 28, wherein the connecting area in the portable therapeutic device includes a convex-shaped section in a body of the portable therapeutic device and the connecting area in the therapeutic subcutaneous access apparatus includes a concave depression to receive the convex-shaped section of the portable therapeutic device.

32. The therapeutic system according to claim 29, wherein the connecting area in the therapeutic subcutaneous access apparatus includes magnetic material to enable magnetic connection with another magnetic material provided in or on the connecting area in the portable therapeutic device.

33. A therapeutic subcutaneous access apparatus for intermittently receiving a portable therapeutic device and adapted for at least one of delivering a therapeutic fluid into the body of a patient and sensing a bodily analyte, the therapeutic subcutaneous access apparatus comprising:
a housing configured to be securable to the skin of a patient, the housing including a well defining a passageway provided within the housing;
a skin-securable cradle having a support surface for securing to the skin of the patient and a recess defined in the support surface for receiving and surrounding the housing to enable connection of the portable therapeutic device to the therapeutic subcutaneous access apparatus; and
a cannula insertable through the well so that at least a portion of the cannula is subcutaneously placed in the body of the patient, wherein:
the cannula is configured for insertion through the well subsequent to securing of the housing to the skin of the patient,
the cannula is configured for rigid connection to the well in a substantially locking configuration upon insertion of the cannula through the well,
the well is configured to tilt relative to a surface of the housing that contacts the skin of the patient when the housing is secured to the skin of the patient, for enabling insertion of the cannula at an angle; and
the well includes a tilting mechanism to control the angle of tilt of the well, the tilting mechanism comprising one or more rods, at least one of the one or more rods having a first end attached to the well and a second end attached to a gear rotatable within a corresponding groove defined in a base of the housing, wherein the groove includes a first section in which the gear can be rotated, a second section into which the gear is placed to lock the gear and well into place, and the second section is narrower than the first section.

34. The therapeutic system according to claim 28, further comprising an insertion device comprising means for reducing resultant pain associated with piercing of the skin of the patient when performing subcutaneous insertion of the cannula.

35. The therapeutic system according to claim 28, further comprising an insertion device configured to automatically subcutaneously insert the cannula.

36. The therapeutic system according to claim 35, wherein the insertion device is further configured to automatically retract a penetrating member subsequent to subcutaneous insertion of the cannula.

37. The therapeutic subcutaneous access apparatus according to claim 1, wherein the skin-securable cradle comprises one or more indentations disposed around the recess, and the housing comprises one or more latches disposed around a perimeter of the housing for securing the housing to the one or more indentations of the skin-securable cradle.

* * * * *